(12) United States Patent
Epstein et al.

(10) Patent No.: US 8,512,333 B2
(45) Date of Patent: *Aug. 20, 2013

(54) ANCHORED RF ABLATION DEVICE FOR THE DESTRUCTION OF TISSUE MASSES

(75) Inventors: Gordon Epstein, Pleasanton, CA (US);
Bruce Lee, Pleasanton, CA (US);
Jeffrey M. Cohen, Pleasanton, CA (US);
Adam Hagmann, Pleasanton, CA (US);
Richard Spero, Pleasanton, CA (US)

(73) Assignee: Halt Medical Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/429,921

(22) Filed: May 8, 2006

(65) Prior Publication Data

US 2007/0006215 A1   Jan. 4, 2007

Related U.S. Application Data

(63) Continuation of application No. 11/173,928, filed on Jul. 1, 2005, now Pat. No. 8,080,009.

(51) Int. Cl.
*A61B 18/14* (2006.01)

(52) U.S. Cl.
USPC ................ 606/41; 606/48; 607/101

(58) Field of Classification Search
USPC ............... 606/41–50; 607/101–102
See application file for complete search history.

(56) References Cited

U.S. PATENT DOCUMENTS

| | | | |
|---|---|---|---|
| 35,330 A | 5/1862 | Silvester | |
| 3,991,770 A | 11/1976 | LeVeen | |
| 4,016,886 A | 4/1977 | Doss et al. | |
| 4,074,718 A | 2/1978 | Morrison, Jr. | |
| 4,080,959 A | 3/1978 | LeVeen | |

(Continued)

FOREIGN PATENT DOCUMENTS

| DE | 2124684 | * 11/1972 |
|---|---|---|
| WO | 03/090636 A1 | 11/2003 |

OTHER PUBLICATIONS

Bergamini, MD, et al., Laparoscopic radiofrequency thermal ablation: A new approach to symptomatic uterine myomas, American Journal of Obsterics and Gynecology (2005) 192, 768-73, Varese, Italy.

*Primary Examiner* — Michael Peffley
(74) *Attorney, Agent, or Firm* — Handal & Morofsky LLC

(57) ABSTRACT

The inventive ablation element comprises an elongated cannula having a proximal end and a distal end. The cannula defines an internal lumen within the cannula and a cannula axis. A plurality of conductors contained within the lumen, each of the conductors has a proximal end proximate the proximal end of the cannula, and a distal end proximate the distal end of the cannula. A plurality of ablation stylets each has a proximal end and a distal end, and each coupled at the respective proximal end of the stylet to the distal end of a respective conductor, the stylets comprise a deflectable material, the conductors together with their respective stylets being mounted for axial movement. A trocar point defined proximate the distal end of the cannula. A deflection surface positioned between the trocar point and the proximal end of the cannula, the deflection surface being configured and positioned to deflect, in response to axial movement of the stylets in a direction from the proximate end of the cannula to the distal end of the cannula, at least some of the stylets laterally with respect to the cannula axis in different directions along substantially straight paths, the paths defining an ablation volume.

25 Claims, 20 Drawing Sheets

(56) References Cited

U.S. PATENT DOCUMENTS

| | | |
|---|---|---|
| 4,095,602 A | 6/1978 | LeVeen |
| 4,119,102 A | 10/1978 | LeVeen |
| 4,140,130 A | 2/1979 | Storm, III |
| 4,154,246 A | 5/1979 | LeVeen |
| 4,230,129 A | 10/1980 | LeVeen |
| 4,285,346 A | 8/1981 | Armitage |
| 4,290,435 A | 9/1981 | Waggott |
| 4,303,636 A | 12/1981 | Gordon |
| 4,346,715 A | 8/1982 | Gammell |
| 4,375,220 A | 3/1983 | Matvias |
| 4,545,368 A | 10/1985 | Rand et al. |
| 4,565,200 A | 1/1986 | Cosman |
| 4,676,258 A | 6/1987 | Inokuchi et al. |
| 4,709,701 A | 12/1987 | Weber |
| 4,773,864 A | 9/1988 | Holt |
| 4,823,791 A | 4/1989 | D'Amelio et al. |
| 4,881,543 A | 11/1989 | Trembly et al. |
| 4,887,614 A | 12/1989 | Shirakami et al. |
| 4,955,884 A | 9/1990 | Grossi et al. |
| 4,962,761 A | 10/1990 | Golden |
| 5,003,991 A | 4/1991 | Takayama et al. |
| 5,007,908 A | 4/1991 | Rydell |
| 5,010,897 A | 4/1991 | LeVeen |
| 5,099,756 A | 3/1992 | Franconi et al. |
| 5,151,101 A | 9/1992 | Grossi et al. |
| 5,190,517 A | 3/1993 | Zieve et al. |
| 5,190,541 A | 3/1993 | Abele et al. |
| 5,234,004 A | 8/1993 | Hascoet et al. |
| 5,257,451 A | 11/1993 | Edwards et al. |
| 5,273,535 A | 12/1993 | Edwards et al. |
| 5,275,162 A | 1/1994 | Edwards et al. |
| 5,282,797 A | 2/1994 | Chess |
| 5,293,863 A | 3/1994 | Zhu et al. |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,322,503 A | 6/1994 | Desai |
| 5,328,467 A | 7/1994 | Edwards et al. |
| 5,334,193 A | 8/1994 | Nardella |
| 5,342,357 A | 8/1994 | Nardella |
| 5,348,554 A | 9/1994 | Imran et al. |
| 5,363,861 A | 11/1994 | Edwards et al. |
| 5,366,490 A | 11/1994 | Edwards et al. |
| 5,368,592 A | 11/1994 | Stern et al. |
| 5,370,675 A * | 12/1994 | Edwards et al. .............. 607/101 |
| 5,370,678 A | 12/1994 | Edwards et al. |
| 5,383,917 A | 1/1995 | Desai et al. |
| 5,385,544 A | 1/1995 | Edwards et al. |
| 5,398,683 A | 3/1995 | Edwards et al. |
| 5,403,311 A | 4/1995 | Abele et al. |
| 5,409,453 A | 4/1995 | Lundquist et al. |
| 5,423,807 A | 6/1995 | Milder |
| 5,423,808 A | 6/1995 | Edwards et al. |
| 5,423,811 A | 6/1995 | Imran et al. |
| 5,433,708 A | 7/1995 | Nichols et al. |
| 5,435,805 A | 7/1995 | Edwards et al. |
| 5,437,662 A | 8/1995 | Nardella |
| 5,454,782 A | 10/1995 | Perkins |
| 5,456,662 A | 10/1995 | Edwards et al. |
| 5,458,596 A | 10/1995 | Lax et al. |
| 5,458,597 A | 10/1995 | Edwards et al. |
| 5,462,521 A | 10/1995 | Brucker et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,531,677 A | 7/1996 | Lundquist et al. |
| 5,536,267 A * | 7/1996 | Edwards et al. .............. 606/41 |
| 5,540,655 A | 7/1996 | Edwards et al. |
| 5,542,915 A | 8/1996 | Edwards et al. |
| 5,542,916 A | 8/1996 | Hirsch et al. |
| 5,542,928 A | 8/1996 | Evans et al. |
| 5,545,161 A | 8/1996 | Imran |
| 5,545,171 A | 8/1996 | Sharkey et al. |
| 5,545,193 A | 8/1996 | Fleischman et al. |
| 5,546,267 A | 8/1996 | Frederiksen et al. |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,560,358 A | 10/1996 | Arnold et al. |
| 5,562,703 A | 10/1996 | Desai |
| 5,582,610 A | 12/1996 | Grossi et al. |
| 5,599,345 A * | 2/1997 | Edwards et al. .............. 606/41 |
| 5,662,680 A | 9/1997 | Desai |
| 5,672,173 A | 9/1997 | Gough et al. |
| 5,672,174 A | 9/1997 | Gough et al. |
| 5,683,384 A * | 11/1997 | Gough et al. .............. 606/41 |
| 5,728,143 A | 3/1998 | Gough et al. |
| 5,759,162 A | 6/1998 | Oppelt et al. |
| 5,782,827 A | 7/1998 | Gough et al. |
| 5,810,804 A * | 9/1998 | Gough et al. .............. 606/41 |
| 5,827,276 A * | 10/1998 | LeVeen et al. .............. 606/41 |
| 5,911,036 A | 6/1999 | Wright et al. |
| 5,921,982 A * | 7/1999 | Lesh et al. .............. 606/41 |
| 5,935,123 A | 8/1999 | Edwards et al. |
| 5,979,453 A | 11/1999 | Savage et al. |
| 6,002,968 A | 12/1999 | Edwards |
| 6,036,689 A | 3/2000 | Tu et al. |
| 6,050,992 A | 4/2000 | Nichols |
| 6,066,139 A | 5/2000 | Ryan et al. |
| 6,071,280 A | 6/2000 | Edwards et al. |
| 6,190,383 B1 | 2/2001 | Schmaltz et al. |
| 6,212,433 B1 | 4/2001 | Behl |
| 6,217,518 B1 | 4/2001 | Holdaway et al. |
| 6,221,071 B1 * | 4/2001 | Sherry et al. .............. 606/41 |
| 6,254,601 B1 | 7/2001 | Burbank et al. |
| 6,312,429 B1 | 11/2001 | Burbank |
| 6,355,033 B1 | 3/2002 | Moorman et al. |
| 6,468,273 B1 | 10/2002 | Leveen et al. |
| 6,575,967 B1 | 6/2003 | Leveen et al. |
| 6,575,969 B1 | 6/2003 | Rittman, III et al. |
| 6,837,887 B2 | 1/2005 | Woloszko et al. |
| 6,840,935 B2 | 1/2005 | Lee |
| 6,974,455 B2 * | 12/2005 | Garabedian et al. .............. 606/41 |
| 2003/0125729 A1 | 7/2003 | Hooven et al. |
| 2003/0130711 A1 | 7/2003 | Pearson et al. |
| 2003/0199868 A1 | 10/2003 | Desai et al. |
| 2004/0215182 A1 | 10/2004 | Lee |
| 2004/0254572 A1 | 12/2004 | McIntyre et al. |
| 2005/0149013 A1 | 7/2005 | Lee |
| 2006/0189972 A1 | 8/2006 | Grossman |

* cited by examiner

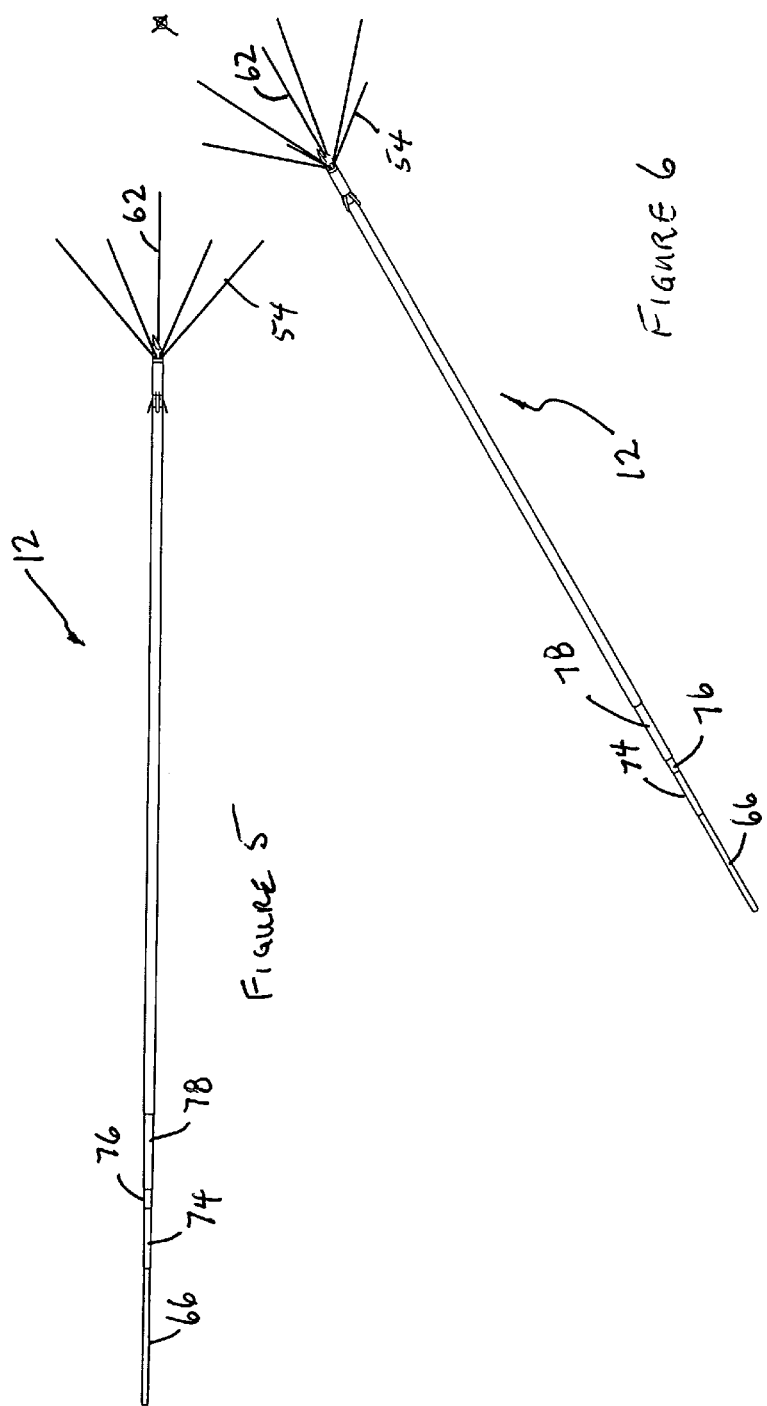

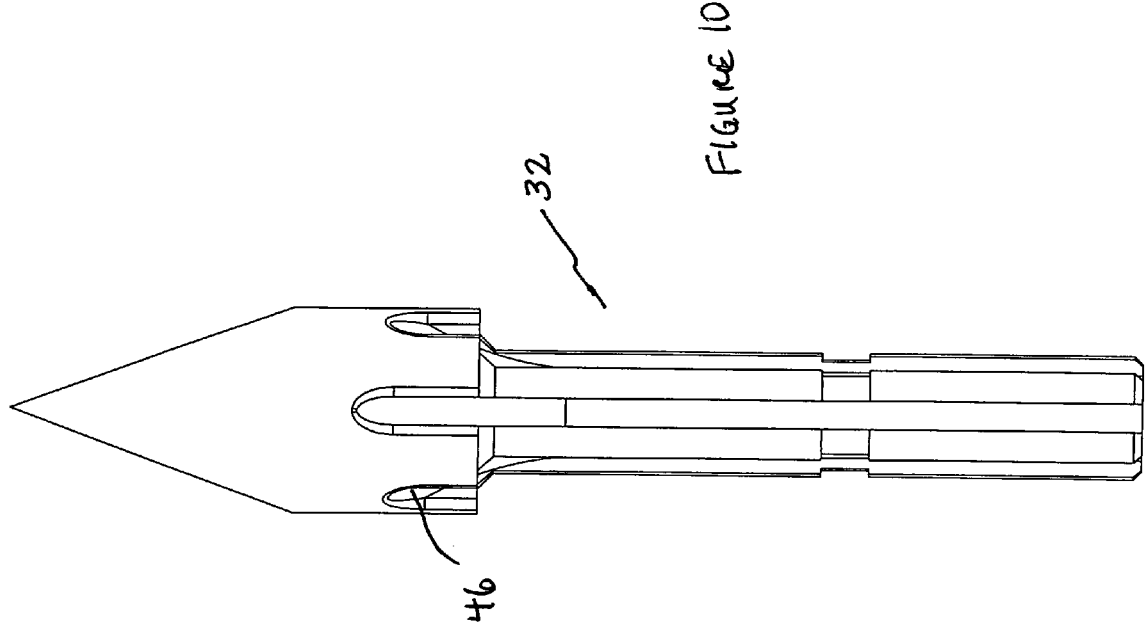

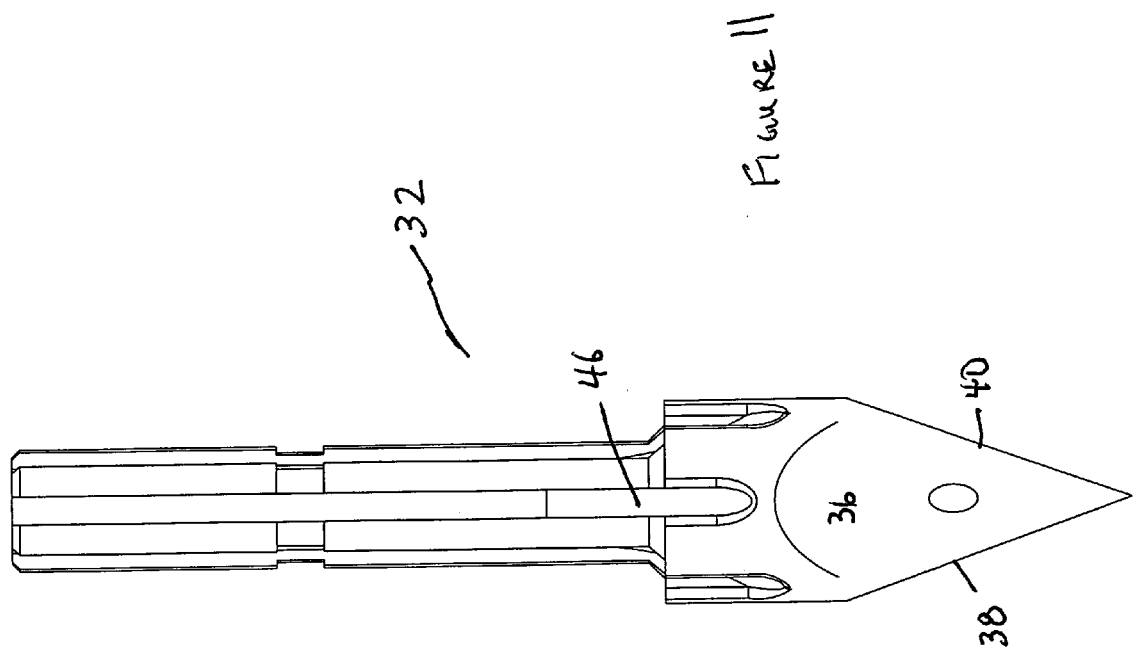

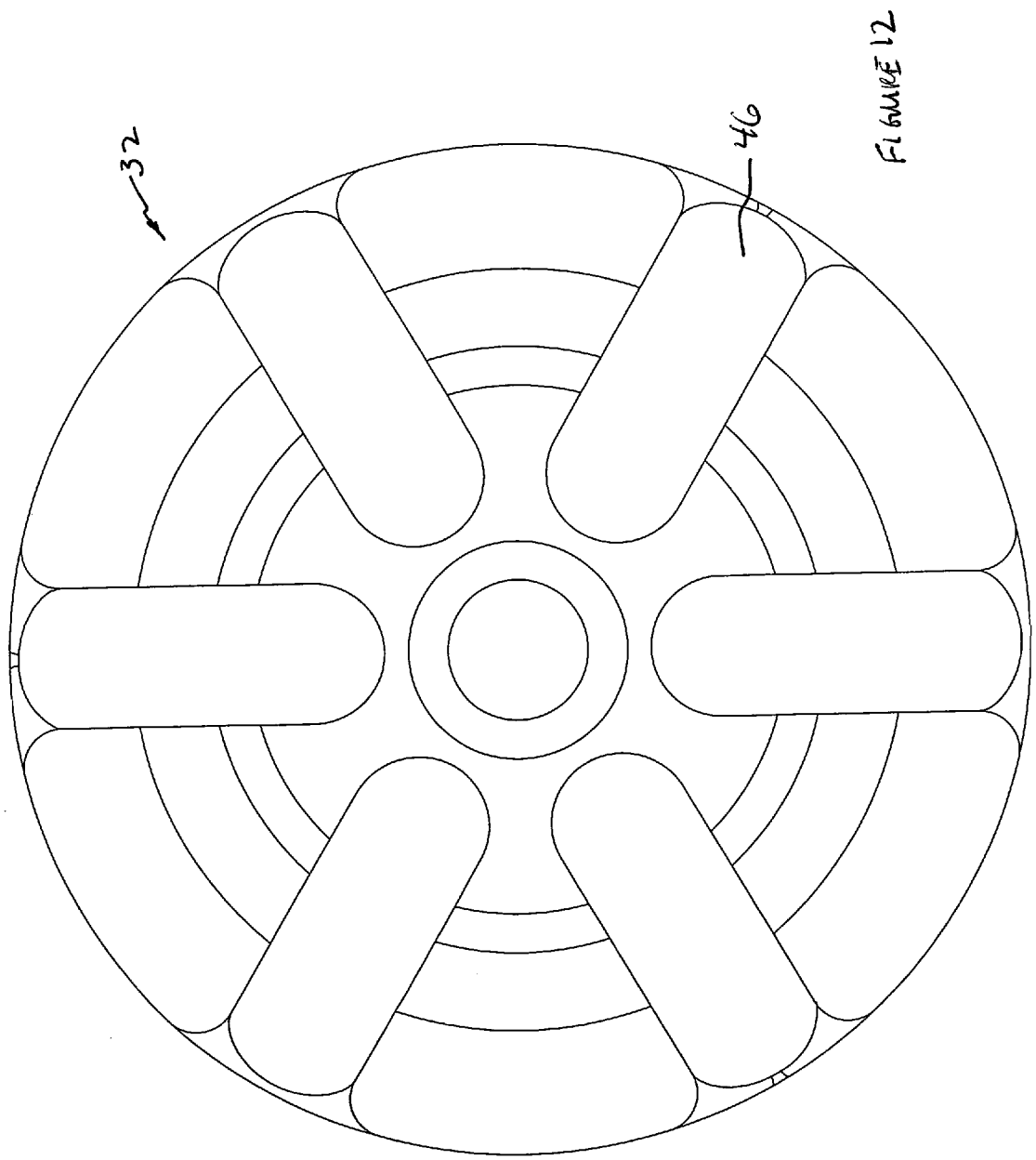

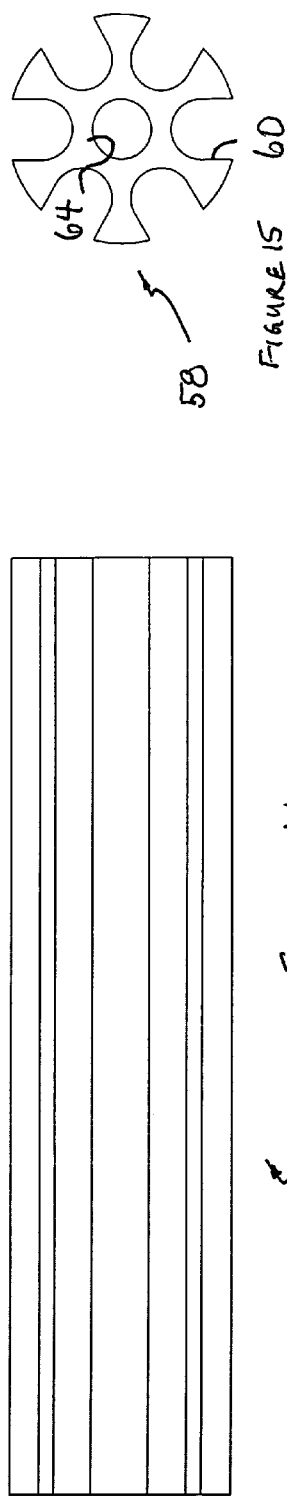
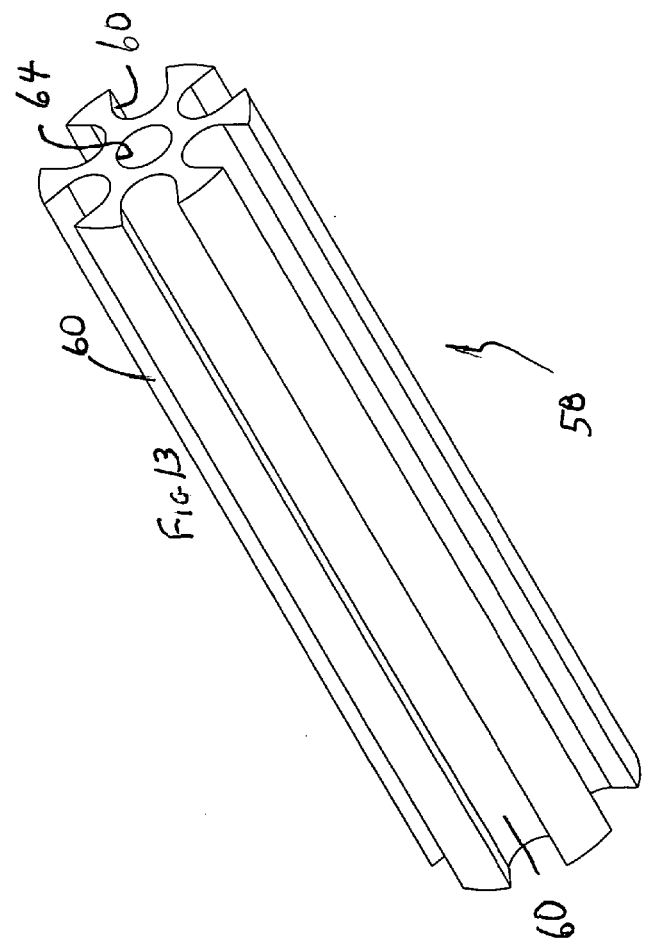

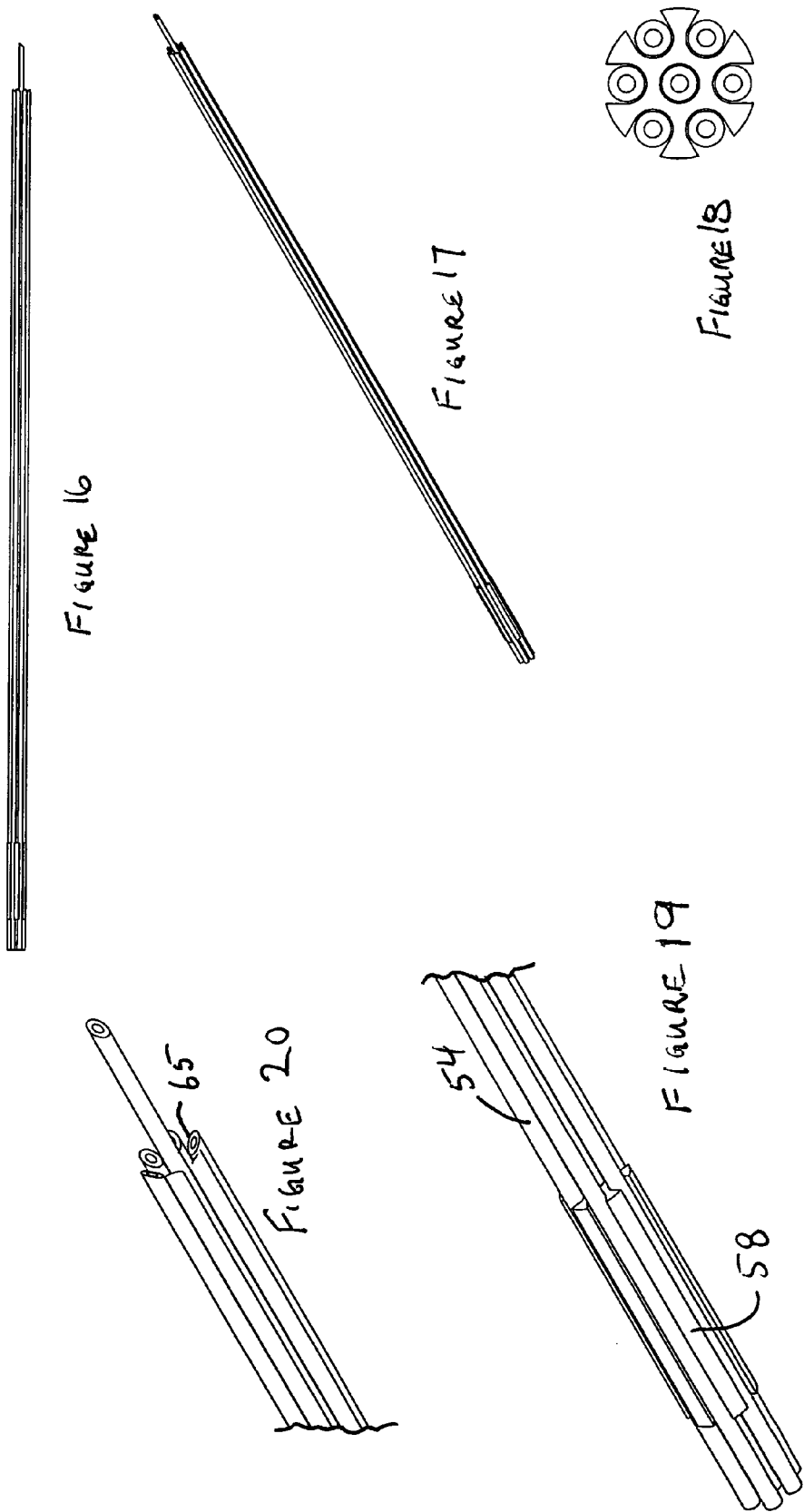

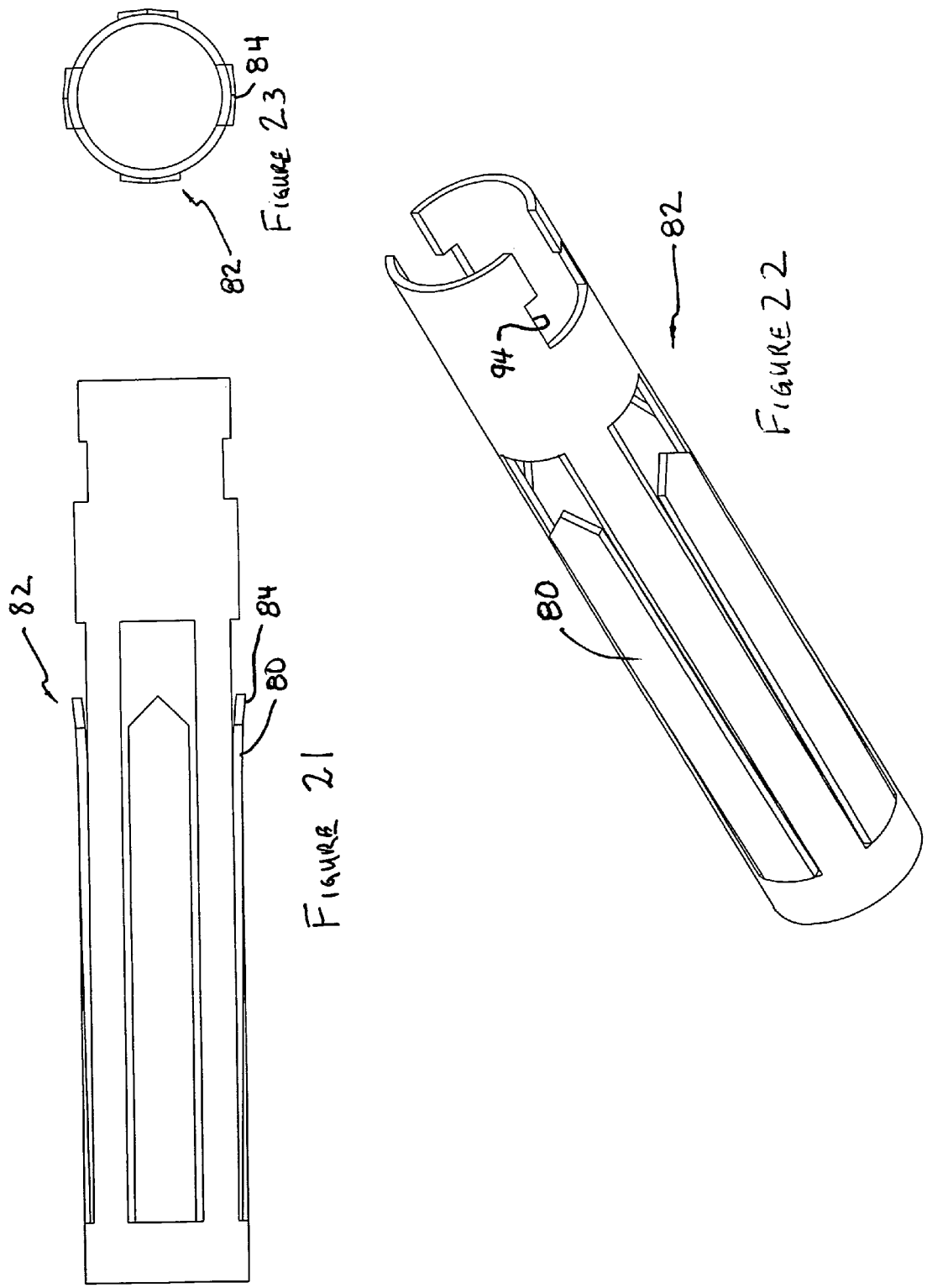

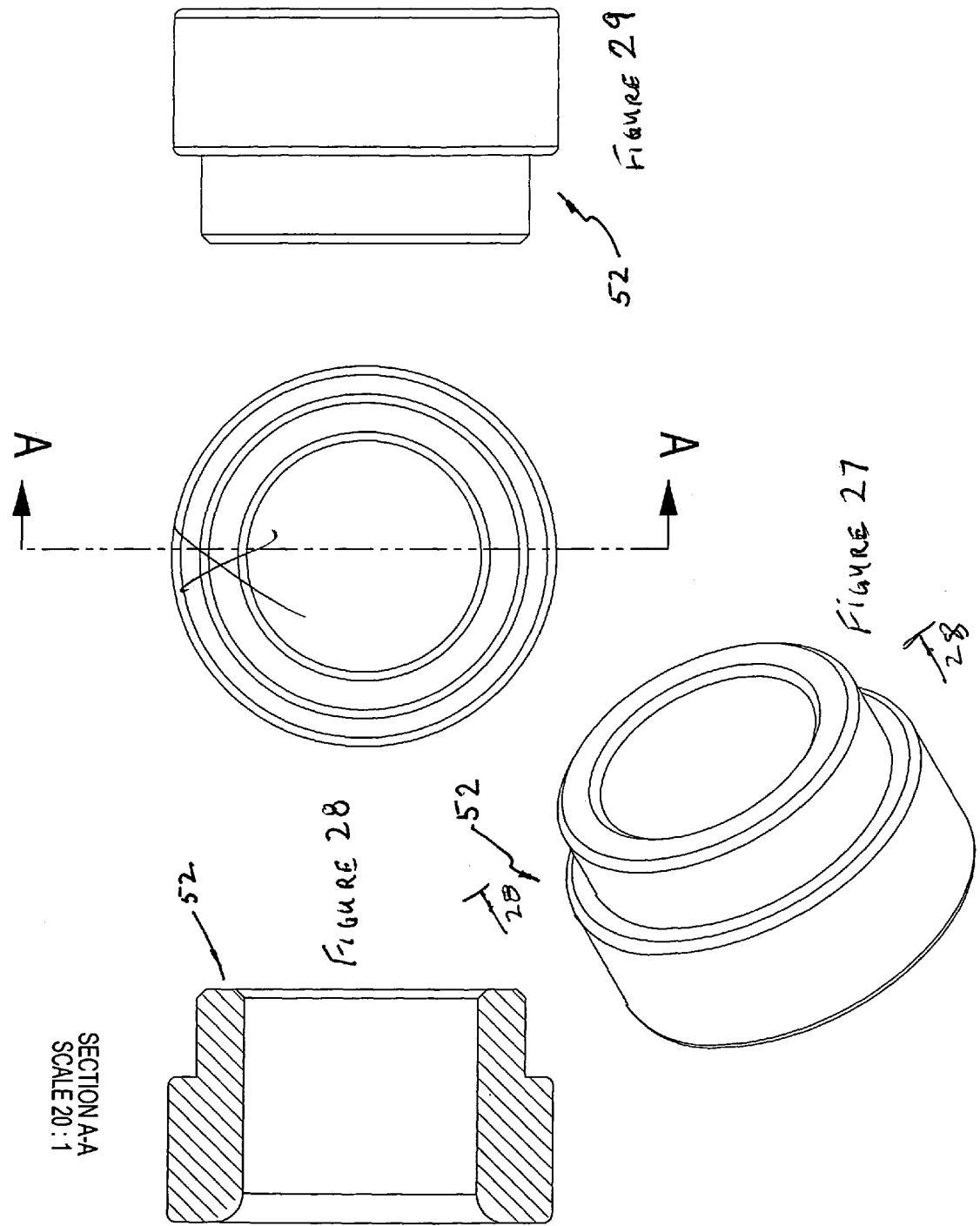

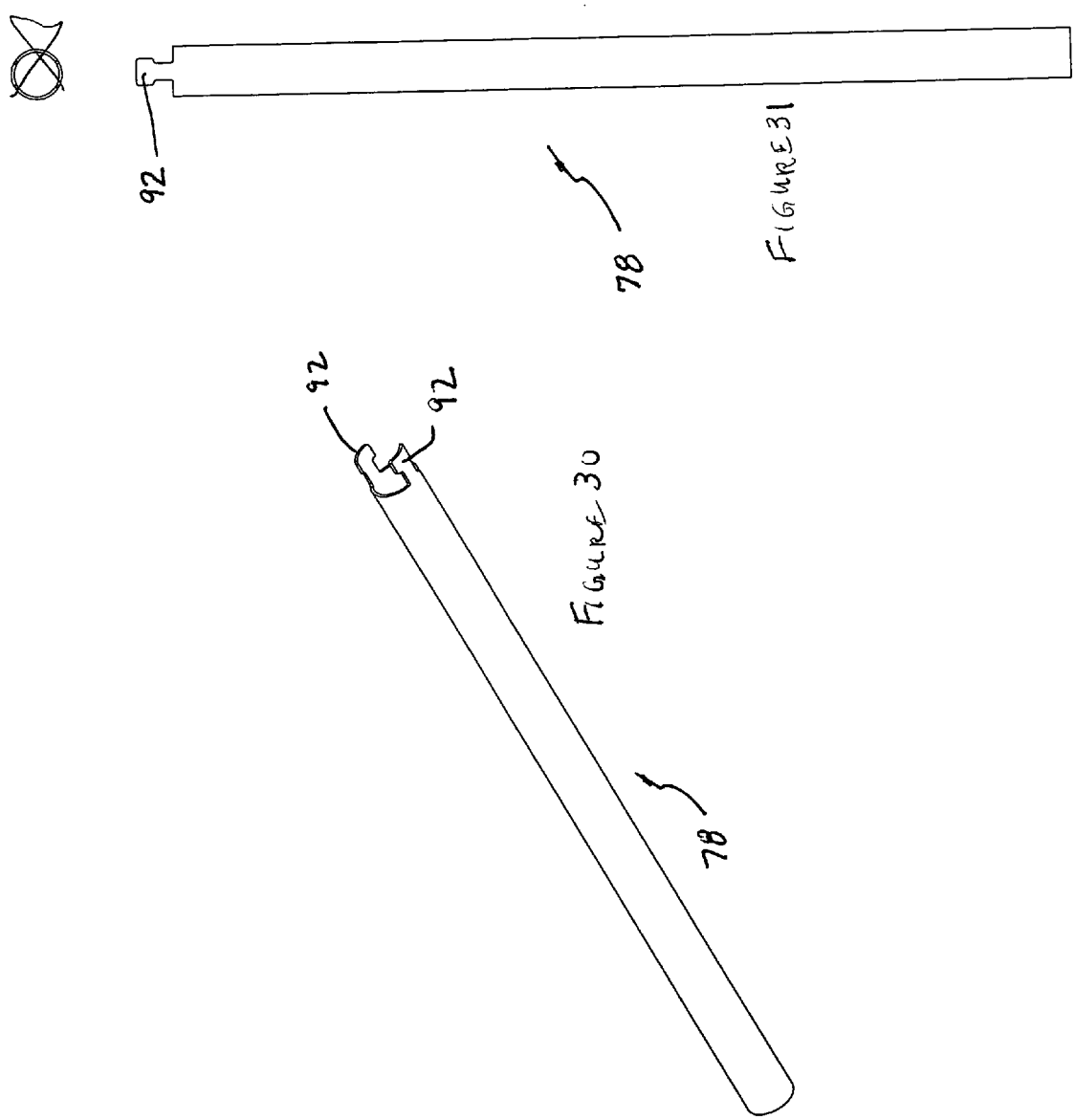

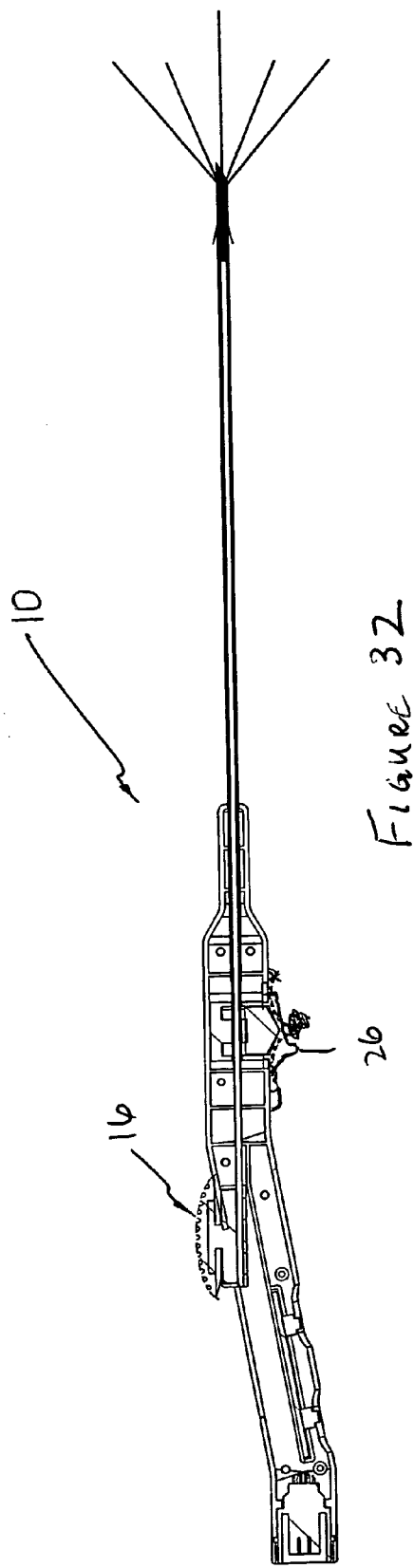

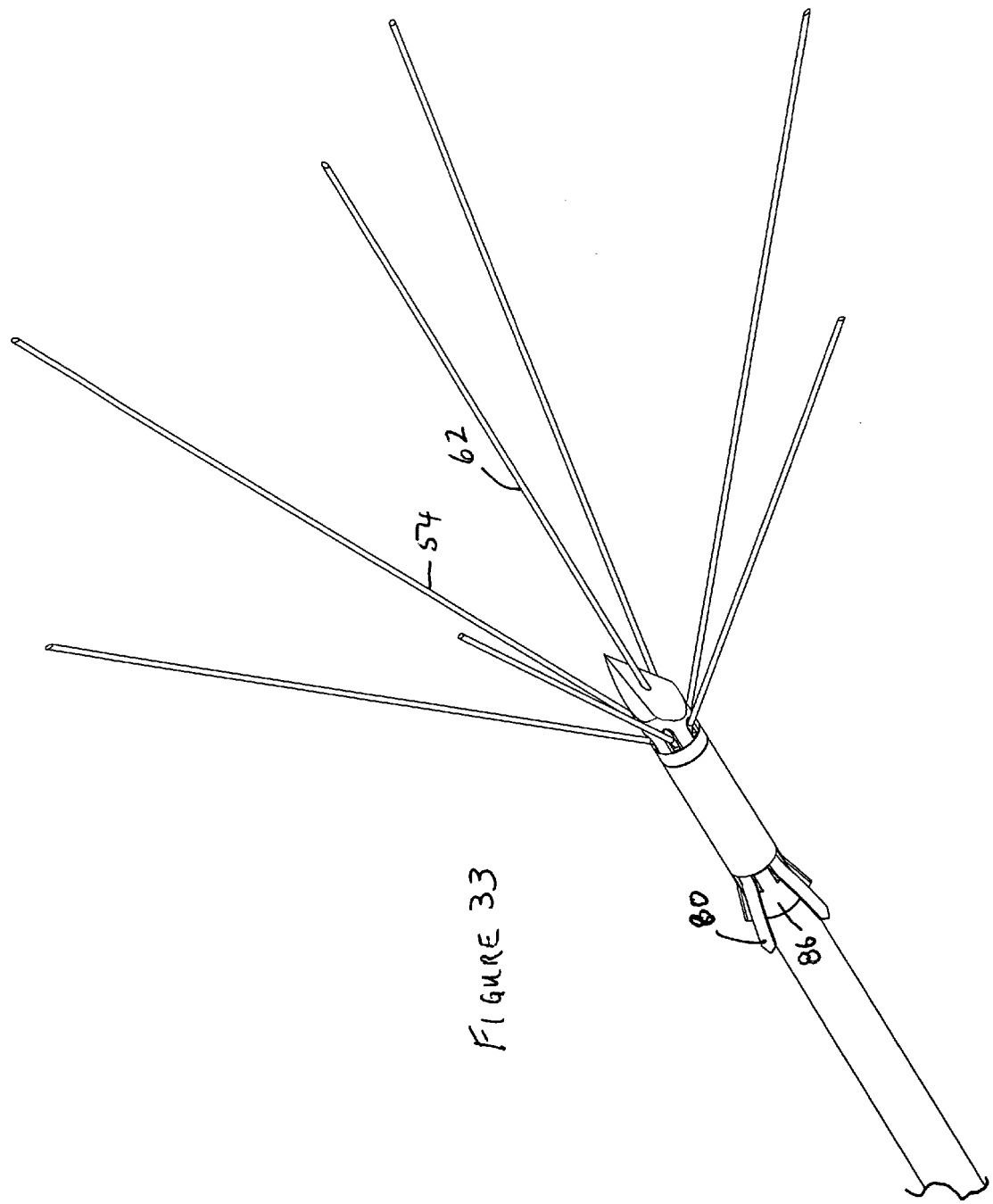

ANCHORED RF ABLATION DEVICE FOR THE DESTRUCTION OF TISSUE MASSES

CROSS REFERENCE TO RELATED APPLICATION

This application is a continuation in part of U.S. patent application Ser. No. 11/173,928, entitled Radio Frequency Ablation Device for the Destruction of Tissue Masses filed on Jul. 1, 2005, now U.S. Pat. No. 8,080,009 the disclosure of which is incorporated by reference.

BACKGROUND

In the United States, approximately 230,000 women have hysterectomies annually. The primary reason for performing a hysterectomy is the presence of uterine fibroids. These fibroids grow in the wall of the uterus and may range in size up to several inches across. In the United States alone, there are more than six million women with uterine fibroid symptoms who prefer to suffer, rather than endure the risks and inconveniences associated with major surgery, especially a major surgery that results in infertility. Outside of the United States, the situation is much the same, with millions of women suffering with fibroids in need of a safe alternative to hysterectomy.

Recently, another treatment option (uterine artery embolization) has been introduced. Generally, this procedure involves embolization of the arteries which feed the urine fibroid. This results in cutting off the blood supply to the fibroid and the shrinkage of the fibroid over time. However, the unacceptably high rate of complications severely limits its appeal to patients.

Myomectomy, each generally involves the surgical removal of the fibroid through the use of classical surgical procedures, is another treatment option. However, due to its high rate of complications and long recovery time, this option is also not very appealing to patients. Typical complications involve risk of infection, relatively severe postsurgical pain, damage to the uterus and other risks normally associated with such types of surgery. Moreover, such damage may be relatively subtle and may only come to light when the uterus begins to swell in pregnancy and ruptures at a weak point created during the surgery, resulting in loss of the fetus.

Still another alternative to treat the discomfort associated with uterine fibroids is the removal of the endometrium which lines the uterus. However, this procedure results in infertility.

In an attempt to address these issues, an RF ablation probe of the type used to treat tumors in the human liver by hyperthermia has been successfully demonstrated to substantially shrink or eliminate uterine fibroids.

See, for example, U.S. Pat. No. 6,840,935 issued to Lee on Jan. 11, 2005, the disclosure of which is incorporated herein by reference. In that patent a method for treating pelvic tumors, such as uterine leiomyomata, includes inserting an ablation apparatus into a pelvic region and positioning the ablation apparatus either proximate to or into a pelvic tumor. The method further includes using a laparoscope and an imaging device, such as an ultrasound machine, to confirm the location of the pelvic tumor and placement of the ablation apparatus. An ablation apparatus with multiple needles or deployable arms that are inserted into the pelvic tumor is disclosed. The method involves delivering electromagnetic energy or other energy through the ablation apparatus to the pelvic tumor to induce hyperthermia and ablate the tumor.

The particular device disclosed for ablating the tumor in U.S. Pat. No. 6,840,935 is of the type disclosed in U.S. Pat. No. 5,728,143, issued to Gough et al. on Mar. 17, 1998. Generally, that device comprises a plurality of resilient springy RF ablation antennae, or stylets, which are preformed with a curved configuration which they assume after exiting a sharp trocar-tipped catheter. The tip of the catheter is deployed in uterine fibroid tissue to be destroyed. The stylets are then deployed into the tissue to be destroyed.

Generally, as the antennae exit the trocar tip, they pierce the tissue of the uterine fibroid along curved paths which are defined by the preformed springy shape of the stylet. The deployed stylets with their respective preformed shapes and the positions within which they are deployed thus define the ablation volume. Various shape volumes may be defined by varying the configuration of the curves which are preformed into the different springy stylets convey given trocar-pointed catheter. Such devices are manufactured by Rita Medical Systems of Mountain View, Calif. The hallmark of such devices is that the stylets assume their pre-formed configuration as they emerge from the trocar tip.

SUMMARY OF THE INVENTION

In accordance with the invention, it has been observed that difficulties are encountered in using conventional curved stylet ablation systems. More particularly, it has been discovered that uterine fibroid tissues tend to be difficult to pierce because, unlike other types of tumors, uterine fibroids are comprised of relatively hard muscle-like tissues and the curved stylets tend to deform during deployment. They are thus not very effective in piercing a uterine stylet. To a limited extent, the difficulty of piercing the fibroid with the curved stylets may be mitigated by advancing very small increments of the ablation stylet into the fibroid, applying radiation to the stylet to induce hyperthermia and degrade the physical integrity of the tissue surrounding the stylets. The stylets may then be advanced into the somewhat deteriorated and softened tissue and the application of radiation to the stylets continued to enlarge the physically deteriorated regions of the fibroid. After a time, the process of advancing the stylet to a point where resistance is encountered, and applying energy to the stylet to cause ablation of the urine fibroid tissue is repeated until penetration into the desired destruction of tissue has been achieved, or the stylets have been fully deployed.

At that point, ablation energy is applied to the stylets until the desired degree of tissue ablation has been achieved. If necessary, the trocar point may then be advanced for a repetition of the ablation operation or it may be removed and redeployed in another volume of tissue to be destroyed by the deployment of the stylets.

While the iterative advancement of the stylets, punctuated by relatively long periods of time during which advancement cannot be implemented and the surgeon must wait for the desired degree of deterioration of the tissue into which the antennae will next be advanced, will work to effectively and minimally-invasively ablate a uterine fibroid, the procedure is extremely time-consuming compared to a procedure in which antennae may be fully deployed and radiation applied to a large volume of a uterine fibroid during a single application of RF energy.

Accordingly, while the above procedure has seen some implementation, the time necessary for the procedure has made it relatively expensive and thus it is not available to many individuals. Moreover, the skill required for the performance of the procedure is relatively high, and thus few doctors are able to perform the procedure. Proliferation of this approach is not likely in view of the steep learning curve and the small number of individuals competent to perform this procedure. This has been the case, despite the effectiveness of ablation in destroying uterine fibroid tissue and the attendant absorption of necrotic tissue by the body, resulting in substantial elimination of the fibroid.

Nevertheless, in accordance with the invention, it is believed that a quick and particularly easy to implement RF ablation procedure is provided, which carries a relatively low risk of complications and a lower likelihood, under a typically encountered set of circumstances, that the uterus will be damaged and fail during a subsequent pregnancy.

In accordance with the invention an ablation element comprises an elongated cannula having a proximal end and a distal end. The cannula defines an internal lumen within the cannula and a cannula axis. A trocar point is positioned proximate the distal end of the cannula. A conductor is contained within the cannula. But conductor has a proximal end and a distal end. The distal end of the conductor is proximate the distal end of the cannula. A plurality of ablation stylets each has a proximal end and a distal end, and each coupled at the respective proximal end of the stylet to the distal end of the conductor, the stylets comprise a deflectable material and defined a substantially straight shape. The conductor together with the stylets are mounted for axial movement within the cannula. A deflection surface is positioned between the tip of the trocar point and the proximal end of the cannula. The deflection surface is configured and positioned to deflect, in response to axial movement of the stylets in a direction from the proximate end of the cannula to the distal end of the cannula, at least one of the stylets laterally with respect to the cannula axis in different directions along paths which are substantially straight for that portion of the stylet which has a suited the trocar point. These paths define an ablation volume.

The conductor may be selected from the group consisting of electrical conductors, radio frequency conductors, microwave conductors and optical conductors or light pipes.

Each of the stylets may be configured to assume a substantially straight configuration in the absence of external forces.

An ablation element further comprises a motor member or members coupled to the conductors to drive axial movement of the stylets in directions from the proximal end of the cannula to the distal end of the cannula, and from the distal end of the cannula to the proximal end of the cannula through a plurality of positions. The trocar point may be defined at the distal end of a trocar member, the trocar member having an outside surface, the cannula having an outside surface, the trocar member having a proximal end secured proximate to the distal end of the elongated cannula, and the outside surface of the cannula and the outside surface of the trocar point defining a trocar surface. The trocar member acts as a stylet mandrel to deflect the stylets, which may be electrodes, along paths which are substantially straight after the stylets exit the mandrel into the tissue to be ablated.

The deflection surface comprises a number of ramps defined proximate the proximal end of the trocar point, the distal ends of the stylets being positionable proximate to the ramps and within the trocar surface.

The conductor and the stylets are electrical conductors, and each of the stylets may be configured to assume a substantially straight configuration in the absence of external forces.

The deflection surface comprises a plurality of channels guiding the distal ends of the stylets to the ramps. The cannula may be secured to the trocar member with the outside surface of the cannula proximate to the outside surface of the trocar member.

The ablation element also comprises an anchor mounted for movement between an internal position disposed within the trocar surface and an anchoring position extending laterally from the trocar surface through points external of the lumen; and a drive member disposed within the lumen and coupled to the anchor to drive the anchor between the internal position and the anchoring position.

The anchor comprises at least two pointed members mounted for movement in directions which have vector components which extend away from the axis of the cannula and away from each other. The pointed members also preferably extend in a direction with a vector component that extends in a direction opposite to the direction in which the trocar point extends.

The conductors are driven by a drive mechanism which allows the conductors to move independently. The conductors have a length, a width and a thickness, the width being greater than the thickness, and terminate in a point oriented to allow deflection by the deflection surface. The conductors extend in different directions when they exit the deflection surface and extend to a variable extent.

The conductors are driven by a drive circuit which varies the amount of energy supplied to the stylets and/or the length of the stylets and/or the length of the time during which power is supplied to the stylets and/or the angular orientation of the ablation element (through the variation of ramp deflection angle.

The parameters of stylet length, stylet power, stylet actuation time and/or angular orientation may be controlled by a computer in response to a computer program having an input comprising feedback information from the tissue area being operated on and/or a preset program.

The anchor is mounted for movement between an internal position disposed within the trocar surface and an anchoring position extending laterally from the trocar surface through points external of the lumen. The drive member may be disposed within the lumen and coupled to the anchor to drive the anchor between the internal position and the anchoring position. The desired motive force for advancing the stylets and/or optional anchors may be provided by a finger operated slidably mounted gripping surface which the surgeon uses to manually advance the conductor and the stylets attached to the end of the conductor. The gripping surface may be slidably mounted on a handle within which the proximal end of the trocar is mounted. The anchor comprises at least two pointed members mounted for movement in directions which have vector components which extend away from the axis or the cannula and away from each other.

As alluded to above, the front end of the inventive catheter is a trocar point defined at the distal end of a trocar member. The trocar member has an outside surface. The cannula has an outside surface, and the trocar member has a proximal end secured proximate to the distal end of the elongated cannula. The outside surface of the cannula and the outside surface of the trocar point define the trocar surface. The trocar member bears a plurality of deflection surfaces. The deflection surface comprises a number of ramps defined within the trocar member. The distal ends of the stylets are positionable proximate to the deflection surfaces and within the trocar surface.

In accordance with a particularly preferred embodiment of the invention, it is contemplated that a graphical user interface and a pair of electrical switches, for example a joystick and a pushbutton, will be used to switch between operating parameter options for the inventive catheter which are displayed on a graphical user interface (or other information conveying device such as an audio cue generator). The surgeon navigates a menu, for example, using a joystick looking at or hearing an electronically generated audio signal, such as a voice, presenting various options and selects the desired option by pushing the electrical switch. In principle, this can be done on a single switch incorporating joystick and pushbutton features.

Optionally, the electrical switches which operate the system may be recessed partially or fully in order to minimize the likelihood of unintentional actuation. Additional protection may be provided by requiring two motions within a relatively short period of time in order to achieve a change in the control of the system.

In accordance with a particularly preferred version of the invention, this is achieved by having a human voice present options and acknowledge instructions, which may be given to the system orally using voice recognition technology. This allows the surgeon to operate without having to look away from visual displays guiding the operation, the patient, instruments and so forth, thus removing potential losses of information. A display siumultaeneously displays all relevant information to provide a quicker provision of information to the surgeon.

In accordance with the invention it is contemplated that laser manufacturing techniques may be used to manufacture the anchors and perhaps the anchor deflection surfaces.

Preferably, the point of the trocar is milled to a point with three surfaces. Stylets are milled in the manner of a hypodermic needle. Stylets are oriented to cooperate with the deflection surfaces which deflect them. A cooperating low friction insulator ring, for example, made of Teflon, cooperates with the deflection surfaces to deflect hypotube electrode stylets.

The present invention contemplates the use of rearwardly deployed anchoring stylets which act as retractable barbs for maintaining the position of the trocar point during forward deployment of the radiofrequency (RF) electrode ablation stylets.

In accordance with the present invention, a stylet operating member, optionally a stylet push member, which may be a tube, is positioned on one side of a tubular compression/tension operator, for example on the inside of the compression/tension operator. Similarly, in accordance with the present invention, and anchor member operating member, optionally an anchor pull member, which may be a tube, is positioned on the other side of a tubular compression/tension operator, for example on the outside of the compression/tension operator. Such outside placement is particularly advantageous in the case where the anchoring member is of relatively wide dimension and large size.

In accordance with a preferred embodiment of the invention, the compression tension operator is secured at the proximal end to the handle of the ablation instrument and at the distal end to the anchoring member deflection surface and the hypotube electrode stylet deflection surface.

The invention contemplates a plurality of hypotube electrode stylets which are bound together as a unitary structure and advanced by a single push tube or wire.

It is also contemplated that the inventive instrument will include channels for flushing clean. In accordance with the inventive system, the frequency with which flushing should be performed is minimized through the use of a trocar front face which is substantially closed (except for a single undeflected hypotube which exits the front face of the trocar) and providing for exit of hypotubes through the cylindrical side wall of the trocar point.

In accordance with a particularly preferred embodiment of the invention, the anchor member is separate from the anchor push tube, and is connected it to by mating or other interlocking structure.

Deflection surfaces for both the hypotube stylets and anchors are selected to result in strains in the range of 2% to 8%, preferably about 4%, for example 3.5% to 4.5%, which represents a reasonable compromise between instrument longevity and a relatively large amount of deflection.

An insulation sleeve is positioned between the anchors and the hypotube stylets in order to allow separate electrical actuation and ablation with either or both of the anchors and the hypotube stylets.

The hypotube stylets contain thermocouples which are used to measure the temperature of ablated tissue, thus ensuring that the tissue will be raised to the correct temperature for a sufficient period of time to ablate tissue resulting in the creation of necrotic tissue which may be absorbed by the body.

In accordance with the preferred embodiment of the invention, hypotube stylets are deployed forwardly or distally while anchors are deployed in a proximal direction or rearwardly. Alternatively, the hypotube stylets may be deployed in a proximal direction or rearwardly, while anchors are deployed forwardly or distally.

As compared to a conventional hysterectomy, the present invention is directed to a device for the treatment of uterine fibroids and other tissue masses that meets the needs of women by conserving the uterus and reducing recovery time from 6-8 weeks to 3-10 days.

BRIEF DESCRIPTION OF THE DRAWINGS

FIG. 5 is a plan view of the catheter with seven hypotube ablation electrodes and four anchors deployed;

FIG. 6 is a perspective view of the catheter structure of FIG. 5;

FIG. 10 is a top plan view illustrating a trocar point with deflection surfaces for guiding hypotubes;

FIG. 11 is a bottom plan view illustrating a trocar point with deflection surfaces for guiding hypotubes;

FIG. 12 is a rear view illustrating a trocar point with deflection surfaces for guiding hypotubes;

FIG. 13 is a perspective view illustrating a core for holding a plurality of hypotubes;

FIG. 14 is a side plan view illustrating a core for holding a plurality of hypotubes;

FIG. 15 is a rear view illustrating a core for holding a plurality of hypotubes;

FIG. 16 is a side plan view illustrating a core holding a plurality of hypotubes;

FIG. 17 is a perspective view illustrating a core holding a plurality of hypotubes;

FIG. 18 is a rear view illustrating a core holding a plurality of hypotubes;

FIG. 19 is a perspective detailed view illustrating a core holding a plurality of hypotubes;

FIG. 20 is a perspective detailed view illustrating the tips of a plurality of hypotubes when they are being held in a core as illustrated in FIG. 19;

FIG. 21 is a side plan view illustrating a rearward anchoring member;

FIG. 22 is a perspective view illustrating a rearward anchoring member;

FIG. 23 is an end view illustrating a rearward anchoring member;

FIG. 27 is a perspective view of an insulating ring for insulating the hypotube electrodes from the anchors;

FIG. 28 is a cross-sectional view of an insulating ring for insulating the hypotube electrodes from the anchors along lines 28-28 of FIG. 27;

FIG. 29 is a side view of the insulating ring for insulating the hypotube electrodes from the anchors;

FIG. 30 is a perspective view illustrating the anchor push tube;

FIG. 31 is a side plan view illustrating the anchor push tube in accordance with the present invention;

FIG. 32 is partially cross-sectional view, similar to FIG. 1 illustrating the inventive instrument with anchors and hypotubes deployed;

FIG. 33 is a detail perspective view illustrating deployment of anchors and hypotube ablation stylets.

DETAILED DESCRIPTION OF THE BEST MODE

Figure 1:
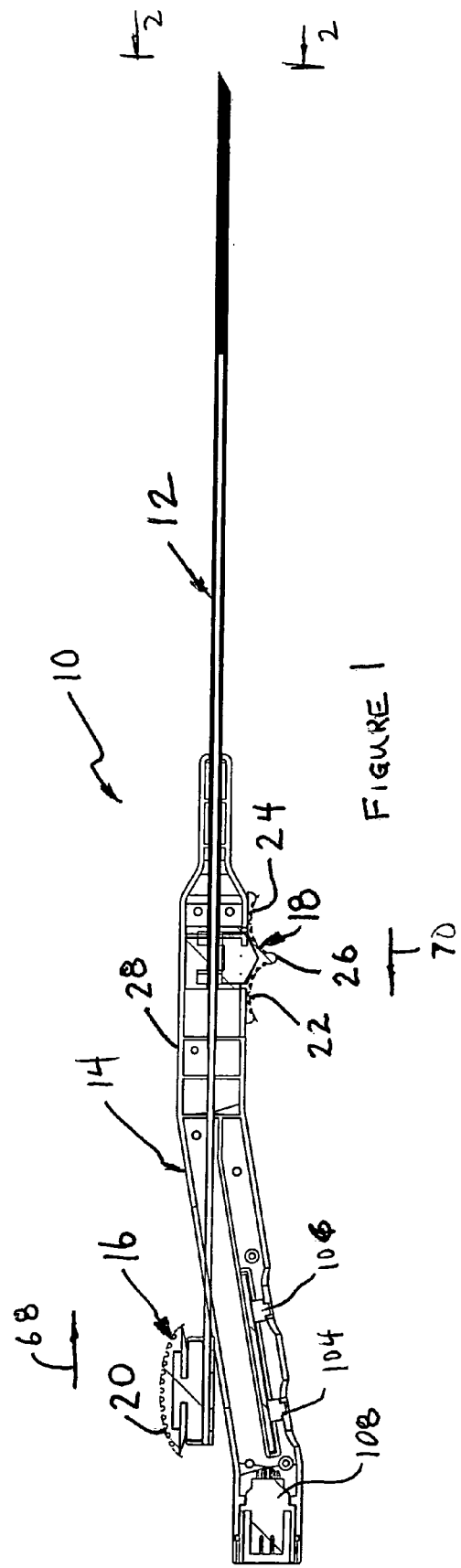
FIG. 1 is a plan view of the multiple antenna ablation device of the invention with the cover removed and partially in cross-section to illustrate its operation.

Referring to FIG. 1, an ablation instrument 10 constructed in accordance with the present invention is illustrated. Instrument 10 comprises a catheter portion 12 and a handle portion 14. Ablation instrument 10 is illustrated with one of the two mating handle halves removed and partially in cross section, in order to reveal its internal parts and workings in connection with the following description.

Figure 2:
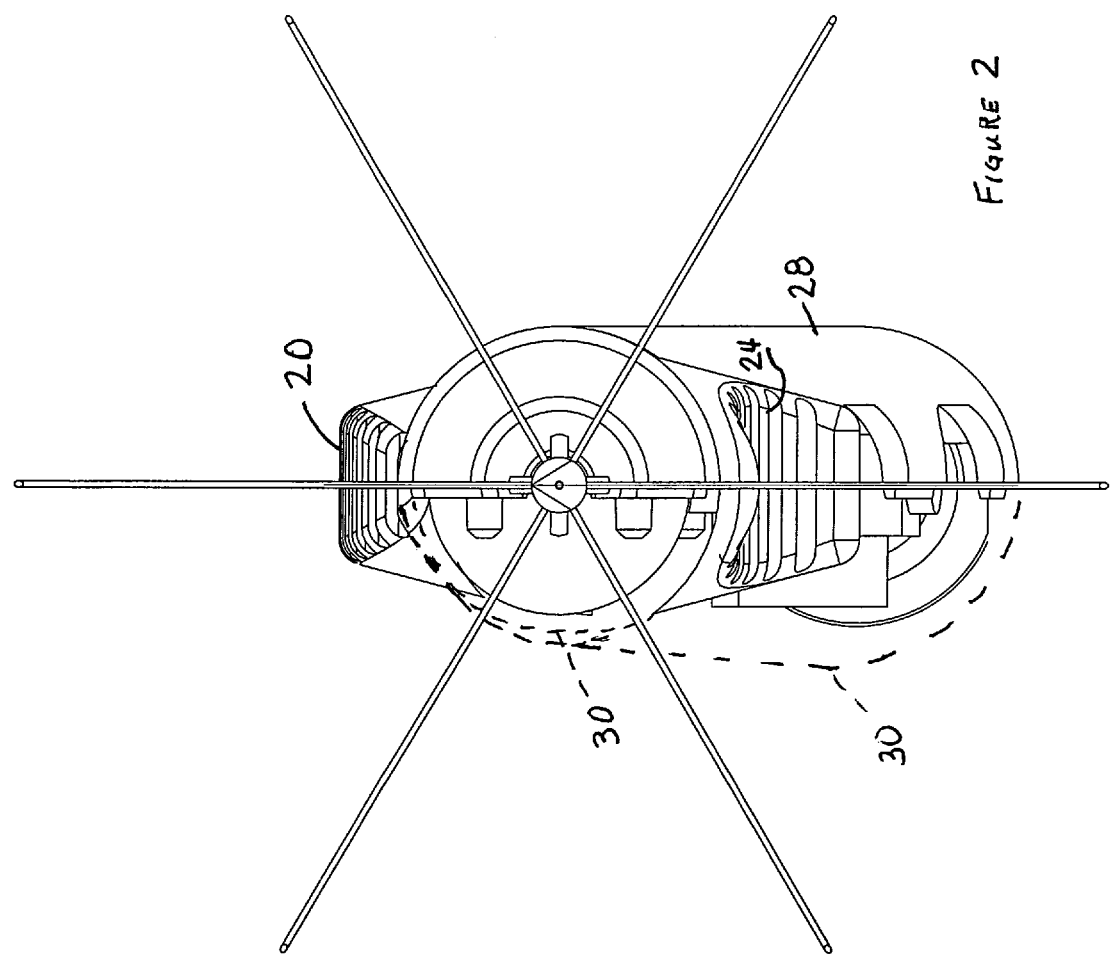
FIG. 2 is a front view of the inventive probe with anchor system of the device along lines 2-2 of FIG. 1, but illustrating the instrument after deployment of the anchor.

Referring to FIGS. 1 and 2, the inventive ablation instrument 10 is illustrated in the fully retracted position suitable for advancement of catheter portion 12 into tissue, for example, tissue to be subjected to ablation by being treated with radiofrequency energy. In this position, the catheter 12 present a simple thin smooth pointed surface well-suited to penetrate healthy tissue while doing minimal damage. At the same time, the sharpness of the point and the relatively stiff, though somewhat flexible, nature of catheter 12 enables accurate steering of the point and control of the path of penetration. In the case of the treatment of uterine fibroids, such steering is achieved largely by manipulation of the uterus coupled with advancement of the catheter 12.

Handle portion 14 includes a pair of actuators namely a stylet actuator 16 and an anchoring actuator 18. Stylet actuator 16 includes a serrated surface 20. Anchoring actuator 18 includes a pair of serrated surfaces, namely an anchor retraction surface 22 and an anchor deployment surface 24. The application of relatively great force is facilitated by a wall 26, against which the thumb or other finger of the surgeon may bear during the respective deployment and retraction phase of an operation performed using the inventive ablation instrument 10. Stylet actuator 16 and anchoring actuator 18 are supported within handle portion 14. Handle portion 14 comprises a left housing half 28 and a right housing half 30 symmetrical in shape to left housing half 28, as illustrated in FIG. 2.

Figure 3:
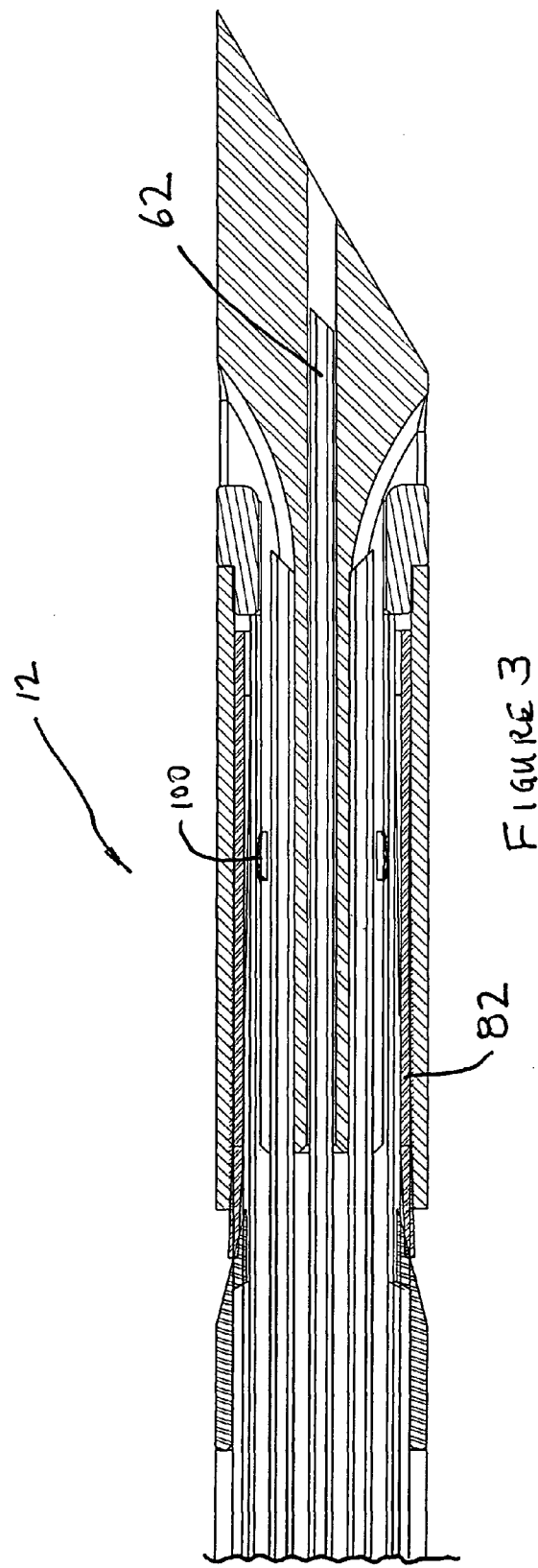
FIG. 3 is a cross-sectional view of the tip of the catheter constructed in accordance with the present invention.
Figure 4:
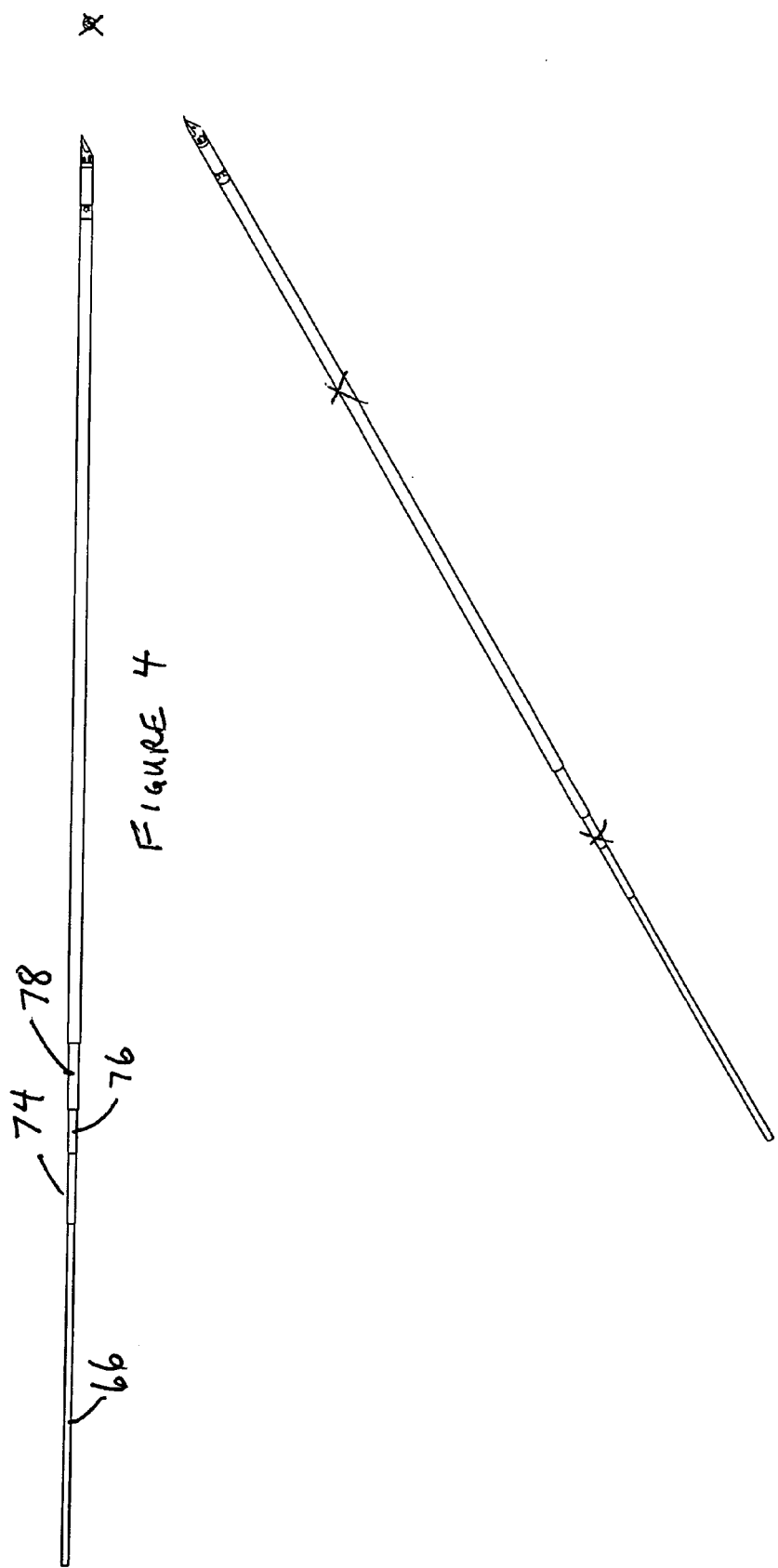
FIG. 4 is a plan view of the apparatus of the present invention with anchors and ablation hypotubes not deployed.

As illustrated in FIGS. 1, 3 and 4, the inventive ablation instrument may be configured in the undeployed state. Alternatively, as illustrated in FIGS. 2, 5, 6 and 7, the inventive ablation instrument 10 may be configured either the anchors or the ablation stylets in a deployed state, or as illustrated in FIGS. 2, 5, 6 and 7 with anchors and stylets both fully deployed.

Figure 7:
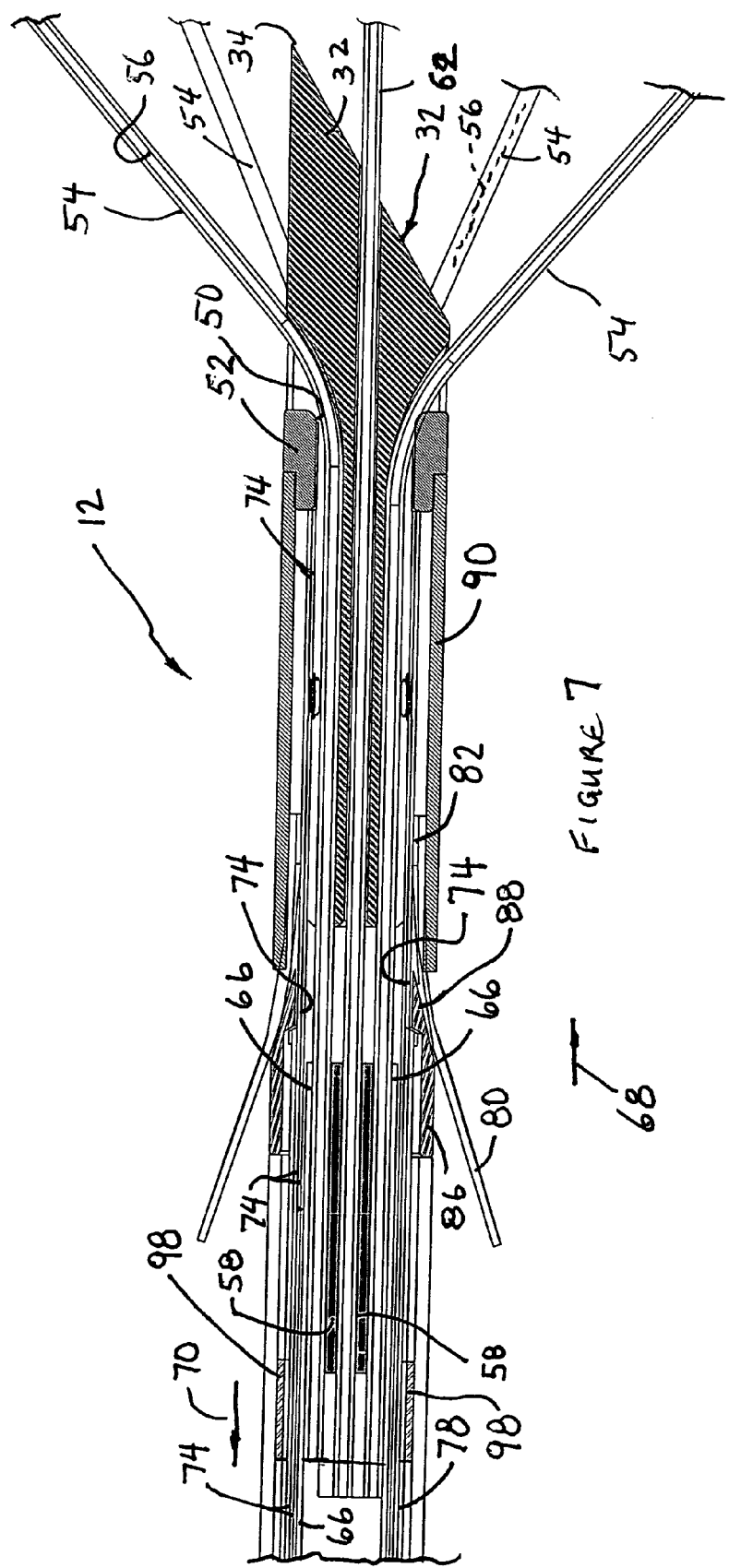
FIG. 7 is a cross-sectional view illustrating deployed hypotubes and anchors.
Figure 8:
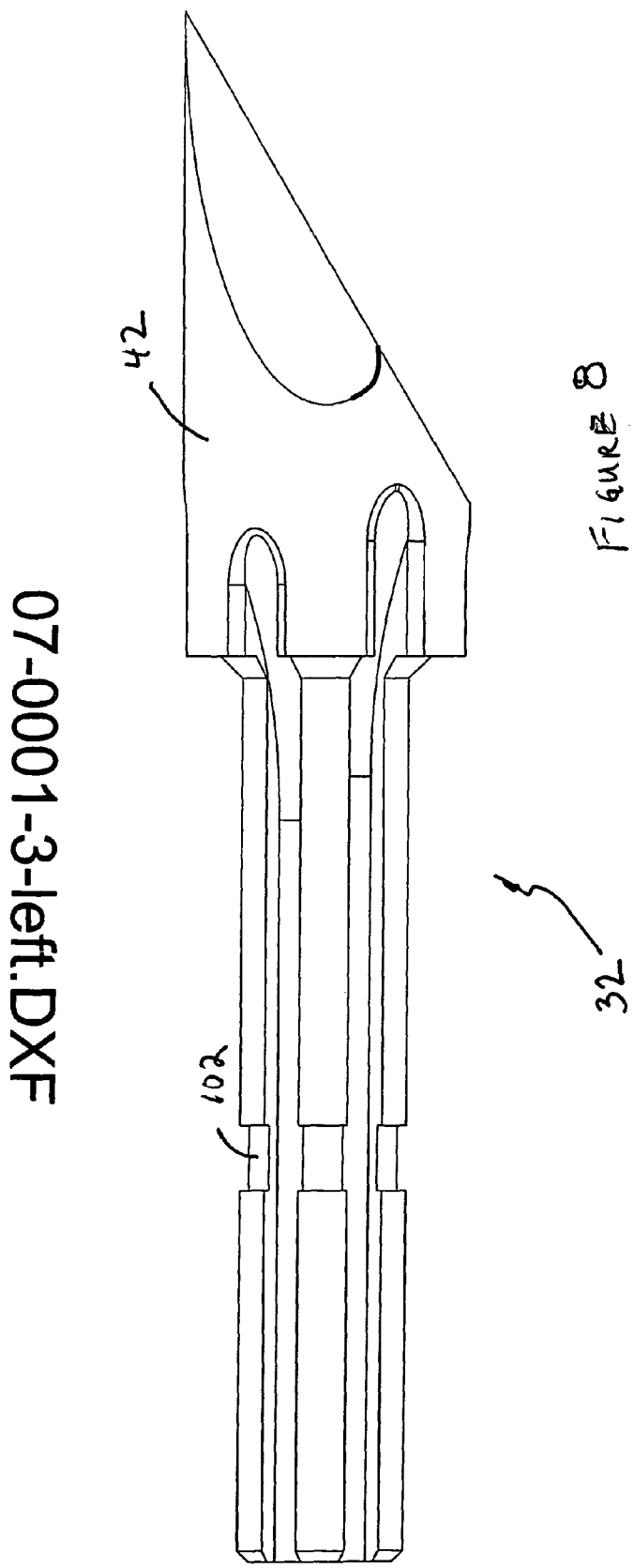
FIG. 8 is a plan view illustrating a trocar point with deflection surfaces for guiding hypotubes.

Referring to FIG. 7, ablation instrument 10 is terminated in a trocar 32, which defines a pointed tip 34. Trocar 32 also functions as an electrode mandrel to deflect the tissue ablation stylets in various directions, as appears more fully below. Trocar 32 is illustrated in FIGS. 8-12. Trocar 32 has a pointed tip 34, defined by bottom surface 36 and side surfaces 38 and 40, as illustrated most clearly in FIG. 8. Surfaces 36, 38 and 40 ground into the distal portion 42 of trocar 32. Trocar 32 also includes a central channel 44 which extends through the length of trocar 32 and is centered on the central axis of trocar 32.

Figure 9:
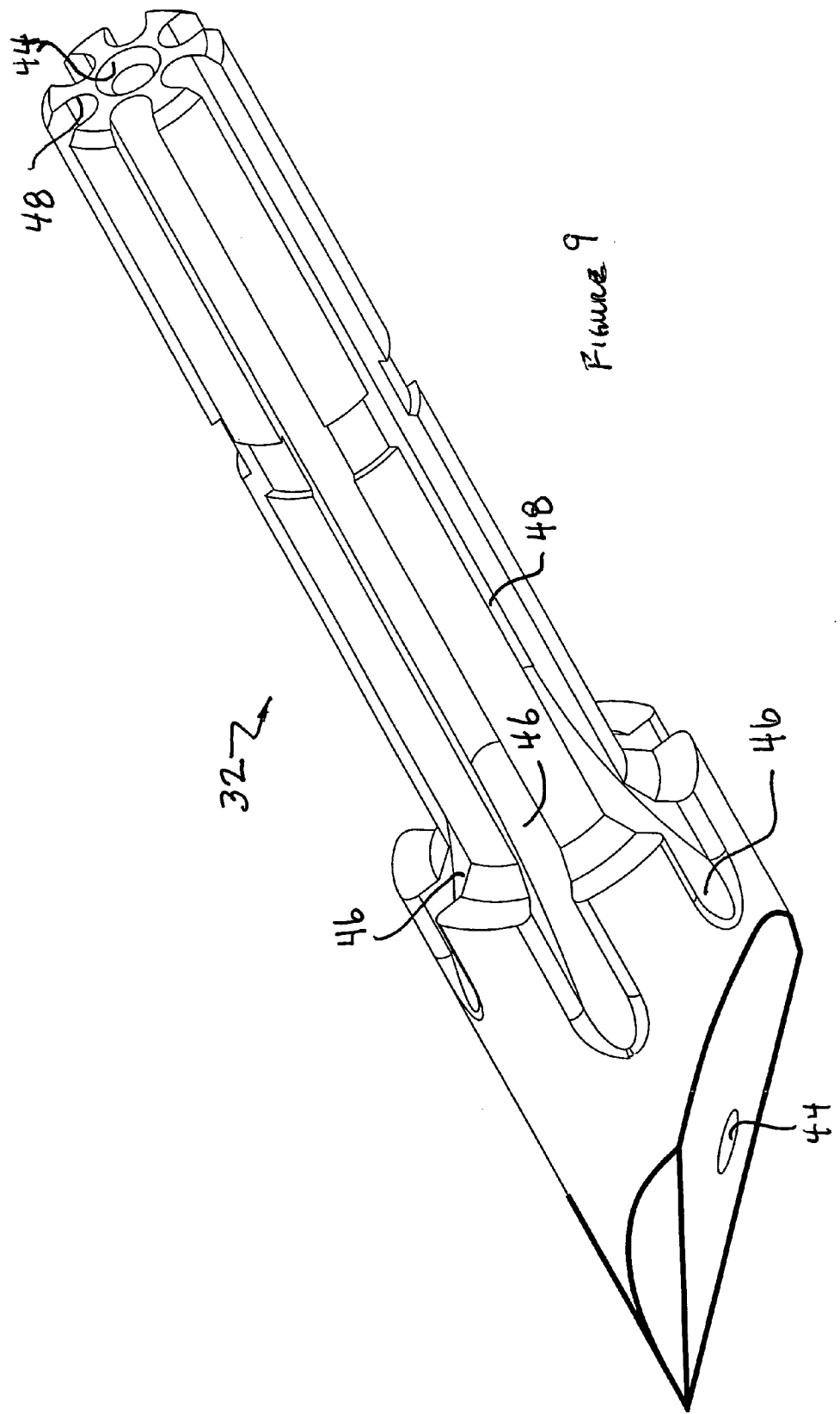
FIG. 9 is a perspective view illustrating a trocar point with deflection surfaces for guiding hypotubes.

A plurality of deflection surfaces 46 are positioned at the end of longitudinal grooves 48, as illustrated in FIG. 9. These surfaces 46 are configured to gently bend the flexible hypotubes which are excited with radiofrequency energy during the ablation of uterine fibroid tissue, causing them to exit catheter 12 and follow substantially straight paths through the tissue to be ablated. During this deflection, the action of deflection surfaces 46 is complemented by the inside curved surface 50 of insulative Teflon deflector ring 52.

In accordance with an especially preferred embodiment of the invention, stylets 54 are made of a nickel titanium alloy instead of stainless steel. In this case, the configuration of deflection surfaces 46 is shaped to maximize the deflection without over straining the nickel titanium alloy material of the stylets. More particularly, in accordance with the preferred embodiment of the invention, surfaces 46 are configured to result in a strain less than eight percent. Strains in the range of 2%-8% will work with strains in the range of about 4%, for example 3.5% to 4.5%, representing an easy to implement commercial solution. Less than 2% strain does not provide appreciable bending with today's technology. Higher performance may be obtained by maintaining a deflection angle which results in a strain of 6-7%. Configuring surface 46 to result in strains approaching 8%, for example 7.5% will maximize deflection and flexibility in design of ablation volume, but will tend to result in quicker degradation of hypotube stylets 54. However, if a particular procedure does not involve a great number of ablations, or the use of several disposable ablation catheters 10 is acceptable, such devices under certain circumstances do present advantages.

The deflection of a plurality of hypotubes 54 is illustrated in FIG. 7. Hypotubes 54 are flexible hollow tubes made of steel or nickel titanium alloy. Hypotubes 54, as well as all other steel parts of the inventive ablation device 10, are preferably, for economic and/or performance reasons, made of stainless steel or other high quality steel, except as indicated herein. The tubes define an internal volume 56 which contains a wire thermocouple, which performs the function of measuring the temperature of the ablated tissue which, over time, allows control of the ablation operation and ensures that the ablated tissue will become necrotic. In FIG. 7, the thermocouples 56 are shown in only one of the tubes for purposes of clarity of illustration.

Hypotubes 54 slidably move in longitudinal grooves 48. Hypotubes 54, which function as ablation electrodes, are mounted on a needle core 58, illustrated in FIGS. 13-15. Needle core 58 includes a plurality of longitudinal grooves 60. Each of six hypotubes 54 is mounted in its respective longitudinal groove 60 and secured in groove 60 by friction or through the use of an adhesive. A seventh hypotube 62 is mounted in a central axial bore 64. The assembly of hypotubes 54 and 62 in needle core 58 is illustrated in FIGS. 16-18. The mounting of hypotubes 54 in needle core 58 is illustrated most clearly in perspective in FIG. 19.

As illustrated most clearly in FIG. 20, hypotubes 54 are preferably oriented with the flat surfaces 65 of their points oriented to slidingly cooperate with deflection surfaces 46 during deployment of the hypotubes. This is done by having the pointed tips of hypotubes 54 radially displaced from the center of catheter 12, which prevents the pointed tips of the hypotubes from digging into deflection surfaces 46.

A flexible steel electrode push tube 66 is disposed around and secured to needle core 58 with the needles mounted in it. Sliding movement of the hypotubes 54 in longitudinal grooves 48 is achieved by movement of electrode push tube 66. Movement in direction 68 causes the deployment of hypotubes 54 and 62. Movement in direction 70 causes retraction of the hypotubes.

Referring to FIGS. 5 and 7, a flexible steel electrode mandrel tube 74 is disposed around and over electrode push tube 66. Flexible steel electrode mandrel tube 74 allows electrode push tube 66 to freely slide within it. This is achieved, despite the relatively large area of the tubes, because the facing surfaces of the tubes are both smooth and because there is a small gap between their facing surfaces, thus minimizing friction. Such gaps allow provision for flushing the instrument clean with water, as is done with prior art devices. A flexible plastic tubular insulative member 76 is disposed around and over electrode mandrel tube 74.

Insulative member 76 isolates electrical radiofrequency ablation energy (carried by push tube 66 for exciting hypotubes 54 and 62) from anchor push tube 78. This allows electrical ablation energy to be optionally applied to anchor push tube 78 to independently cause the anchors 80 on anchor member 82 to apply ablation energy to a different volume than that which is ablated by the electrode stylets 54 and 62. Anchor member 82 is illustrated in FIGS. 21-23. Anchors 80 are cut using a laser from a steel tube to form steel anchor member 82. Each anchor 80 has a tip 84 which is bent radially outwardly to facilitate deflection over anchor mandrel 86 in response to movement of anchor member 82 in the direction of arrow 70.

Figure 25:
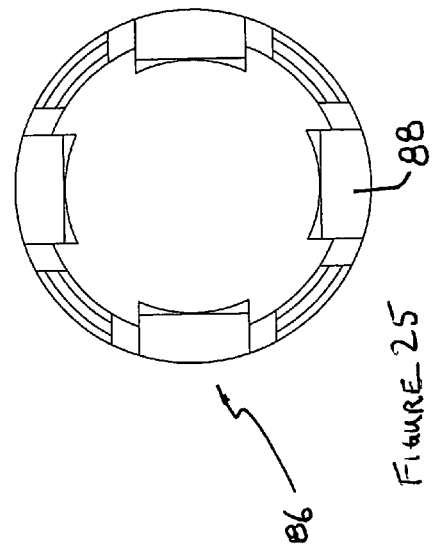
FIG. 25 is an end view illustrating an anchor deflecting mandrel member.
Figure 24:
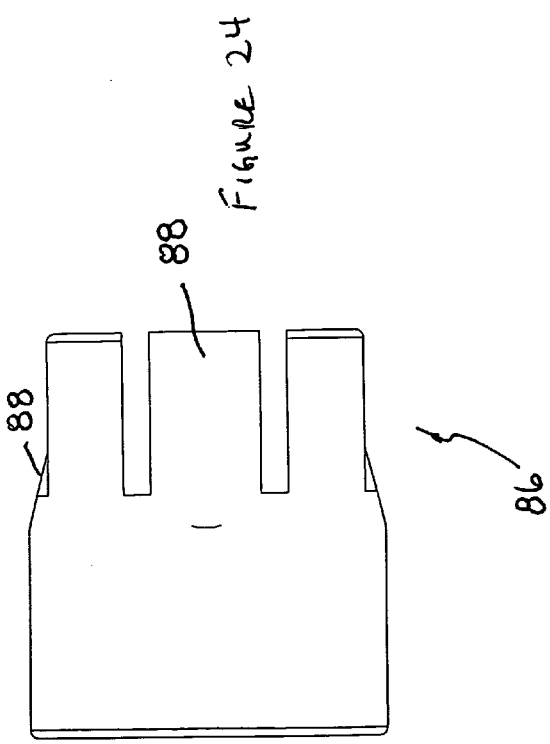
FIG. 24 is a plan view illustrating a rearward anchoring member.
Figure 26:
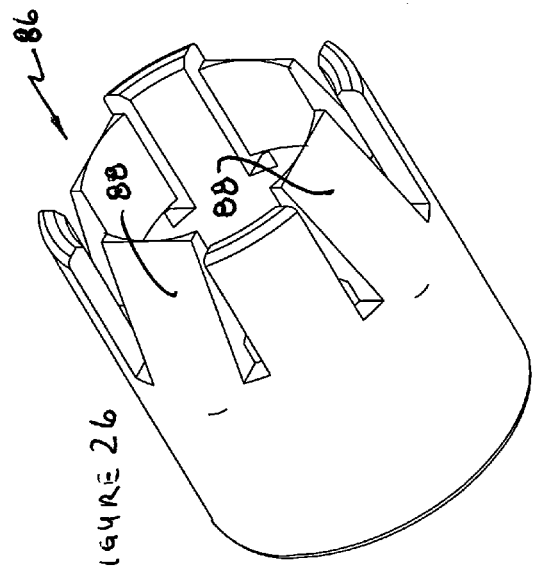
FIG. 26 is a perspective view illustrating an anchor deflecting mandrel member.

Anchor mandrel 86 is illustrated in FIGS. 24-26. Anchor mandrel 86 incorporates a number of deflection surfaces 88, as illustrated most clearly in FIGS. 7 and 26. In accordance with an especially preferred embodiment of the invention, anchor member 82, and thus anchors 80, are made of a nickel titanium alloy instead of stainless steel. Nickel titanium alloy is a preferred material for both anchors 80 and stylets 54.

The configuration of deflection surfaces 88 is shaped to maximize the deflection without over-straining the nickel titanium alloy material of the anchors. More particularly, in accordance with the preferred embodiment of the invention, surfaces 88 are configured to result in a strain less than eight percent. Strains in the range of 2-8% will work with strains in the range of about 4%, for example 3.5 to 4.5%, are less rigorously 3% to 5%, representing an easy to implement commercial solution. Higher performance may be obtained by maintaining a deflection angle which results in a strain of 6-7%. Configuring surface 88 to result in strains approaching 8%, for example 7.5% will maximize deflection and flexibility in design of ablation volume, but will tend to result in quicker degradation of anchors 80. However, if a particular procedure does not involve a great number of ablations, or the use of several disposable ablation catheters 10 is acceptable, such devices under certain circumstances do present advantages.

The structure of the distal end of catheter portion 12 is completed by a steel anchor cover 90, which is supported on, surrounds and is secured to insulating ring 52 whose structure is illustrated in FIGS. 27-29. During deflection, anchors 80 pass between deflection surfaces 88 and the inside surface of steel anchor cover 90.

Anchor push tube 78, illustrated in FIGS. 30 and 31 includes a pair of keys 92 which are shaped like the letter T. Keys 92 mate with slots 94 in anchor member 82. Anchor member 82 and anchor push tube 78 thus act as a unitary member during deployment and retraction of anchors 80, in response to sliding motion of anchor member 82 and anchor push tube 78.

The structure of catheter 12 is completed by outer tube 96 which is secured to handle 14 at one end and secured to a tubular slip ring 98 which slides over anchor push tube 78.

FIG. 1 illustrates the relative positions of anchoring actuator 18, and stylet actuator 16 before deployment of anchors and stylets. This corresponds to FIG. 4.

Electrode mandrel tube 74 is secured at its proximal end to handle 14. At its distal end, electrode mandrel tube 74 is secured to trocar 32, for example by a quantity of epoxy adhesive 100 in the annular groove 102 on trocar 32, as illustrated in FIG. 3. Stylet actuator 16 is secured to electrode push tube 66. Thus, movement in the direction of arrow 68 in FIG. 1 causes the stylets to emerge from the end of the catheter as illustrated in FIGS. 5, 6, 7 and 32. Full deployment of ablation electrodes or stylets 54 and 62 is illustrated most clearly in FIG. 33.

Anchoring actuator 18 is secured to anchor push tube 78. At its distal end, electrode mandrel tube 74 is secured to anchor mandrel 86, for example by a quantity of epoxy adhesive. Accordingly, movement of anchoring actuator 18, in the direction of arrow 70 in FIG. 1, causes the anchors 80 to emerge from the catheter as illustrated in FIGS. 5, 6, 7 and 32. Full deployment of anchors 80 is illustrated most clearly in FIG. 33.

In accordance with the present invention it is contemplated that control of the inventive ablation device 10 will be achieved by one or two electrical switches 104 and 106. Operation of switch 106 will cause the appearance of a menu on a display, for example by axial movement of switch 106 in the manner of a joystick. Transverse movement of switch 106 causes the menu to switch between different menu items, such as controlling ablation time, controlling ablation temperature, or some other parameter. Selection of the desired value for the selected parameter is achieved by transverse motion of switch 106, causing the various values to be displayed on the display. When the desired value is seen on the screen by the surgeon, depression of switch 104 registers that value with the electronic circuit controlling ablation and causes the inventive ablation device 10 to be operated in accordance with the selected parameter.

RF ablation energy, control signals, and temperature measurement signals are coupled from the inventive ablation device 10 to a control unit/RF energy source by a connector 108. In accordance with the present invention, it is contemplated that a conventional radiofrequency energy source such as that used in conventional ablation systems would be employed in conjunction with the inventive ablation device 10.

In accordance with the present invention, cauterization radiofrequency energy may also be applied to trocar 32 during withdrawal of trocar 32 from the patient in order to control loss of blood. It is noted that the nature of the RF signal needed to achieve cautery is different from the nature of an ablation signal. Both of these signals are well defined in the art. Likewise, their generation is also well-known. However, in accordance of the present invention conventional cautery and conventional ablation signals may be used for cautery and ablation, respectively.

Figure 34:
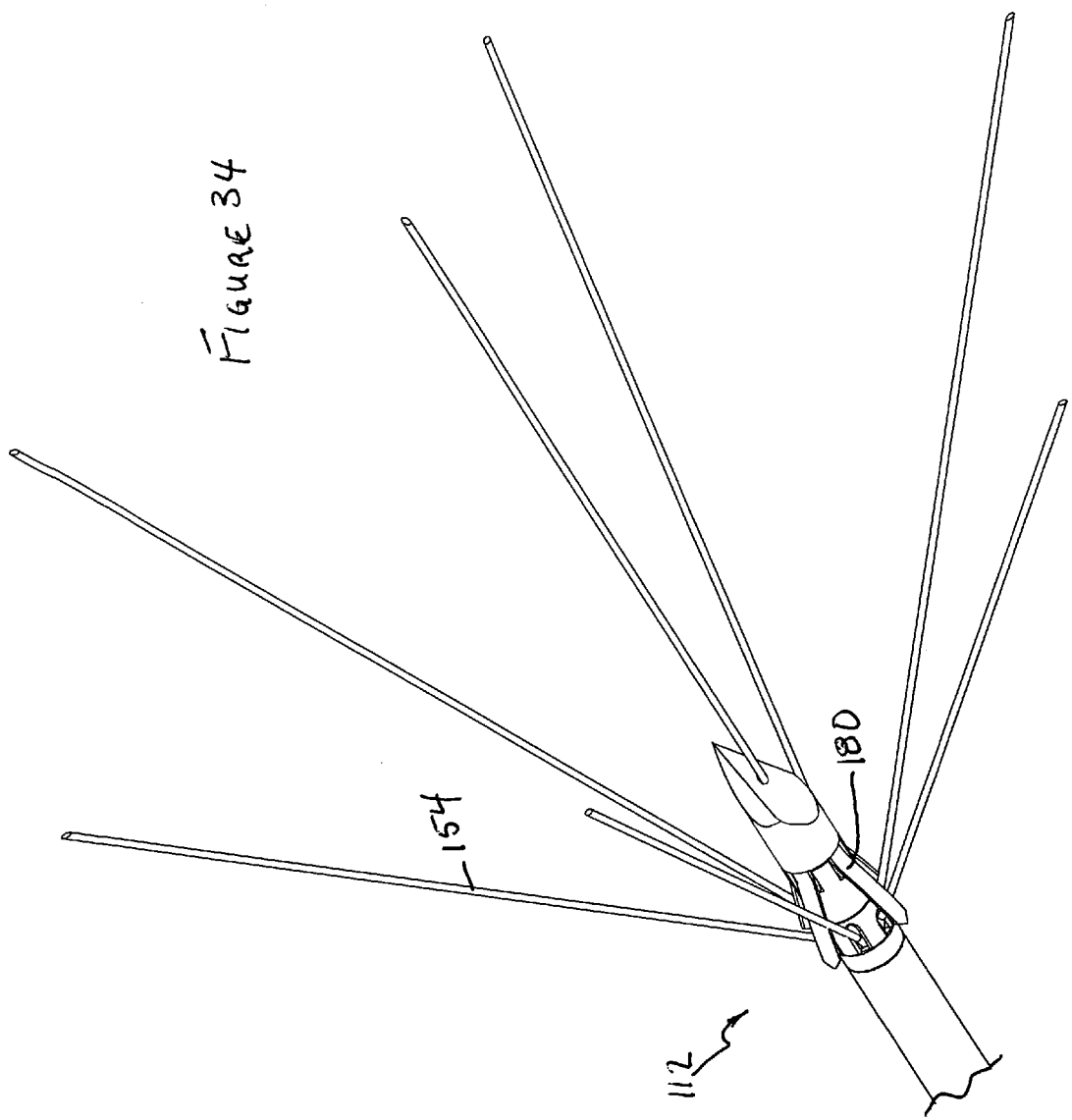
FIG. 34 is a detail perspective view similar to FIG. 33 illustrating full deployment of hypotubes and anchors in an alternative embodiment of the invention.

An alternative embodiment of the inventive catheter 112 is illustrated in FIG. 34. Here anchors 180 are positioned distally of ablation electrodes 154.

While the inventive device has been illustrated for use in the ablation of uterine fibroids, it is understood that this particular implementation is exemplary and that the inventive device may be employed in a wide variety of circumstances. Likewise, while an illustrative embodiment of the invention has been described, it is understood that various modifications to the structure of the disclosed device will be obvious to those of ordinary skill in the art. Such modifications are within the spirit and scope of the invention which is limited and defined only by the appended claims.

The invention claimed is:

1. An ablation instrument, comprising:
    (a) an elongated support member having a proximal portion and a distal portion, said elongated support member defining an elongated support surface, and an elongated support member axis;
    (b) at least one conductor extending along at least a portion of the length of said elongated support member surface and mounted for axial movement of at least a portion of said conductor;
    (c) a plurality of ablation stylets, each of said stylets being made of metal and having an elongated exposed metal distal portion, said exposed metal distal portion having a length roughly commeasurate with the region to be ablated, said stylets being supported proximate the distal portion of said elongated support member, said stylets comprising a resiliently deflectable material, and said stylets being mounted for axial movement of at least a portion of said stylets;
    (d) a head positioned to receive the distal portion of said stylets, said head comprising a head end; and
    (e) open deflection surfaces positioned proximate said head end and proximate said distal portion of said elongated support member, said deflection surfaces being configured and positioned, in response to advancement of said stylets toward said head end, to deflect at least some of said stylets laterally and only forwardly with respect to said elongated support axis causing said stylets to exit said deflection surfaces and move along substantially straight external paths external to said elongated support member and said head.

2. An ablation instrument as in claim 1, further comprising a countersurface cooperating with said deflection surfaces and defining respective countersurface portions in facing spaced relationship to respective ones of said deflection surfaces.

3. An ablation instrument as in claim 2, wherein said countersurface comprises a low friction nonmetallic material.

4. An ablation instrument as in claim 1, wherein said stylets are deflected with a strain between 3.5% and 4.5%.

5. An ablation instrument as in claim 1, wherein said ablation stylets are secured to each other in a unitary structure comprising a support member having a plurality of mounting surfaces each configured to engage a respective ablation stylet.

6. An ablation instrument as in claim 5, wherein said head is a trocar comprising a trocar point and said deflection surfaces comprise a number of ramps defined proximate the proximal end of said trocar point, the distal ends of said stylets being positionable proximate to said ramps.

7. An ablation instrument as in claim 6, wherein said conductor is an electrical conductor, said stylets are electrical conductors, and each of said stylets are configured to assume a substantially straight configuration in the absence of external forces.

8. An ablation instrument as in claim 1, further comprising:
    (g) an anchor mounted for movement between an internal position disposed within said elongated support member and an anchoring position extending laterally from said elongated support member through points external of said lumen.

9. An ablation instrument as in claim 8, wherein said anchor comprises at least two pointed members mounted for movement in directions which have vector components which extend away from the axis of said elongated support member and away from each other.

10. An ablation instrument as in claim 1, wherein said stylets comprise an alloy comprising nickel and titanium alloy.

11. An ablation element as in claim 10, wherein said stylets are secured to each other at least along a portion of their length to form a stylet assembly.

12. An ablation element as in claim 10, further comprising a plurality of anchor members and an anchor member deploying operator mounted for axial movement independent of said at least one conductor.

13. An ablation element as in claim 1, wherein the parameters of stylet length, stylet power, stylet actuation time and/or angular orientation are controlled by a computer in response to a computer program having an input comprising feedback information from the tissue area being operated on and/or a preset program.

14. An ablation element as in claim 1, wherein said head end is a trocar point defined at the distal end of said head, said head comprising a trocar member, said trocar member having an outside surface, said support member comprising a cannula, said cannula having an outside surface, said trocar member having a proximal end secured proximate to the distal end of said elongated cannula, and the outside surface of said cannula and the outside surface of said trocar point defining a trocar surface, and wherein said stylets are made of a nickel titanium alloy and are deflected to a strain of less than 8%.

15. An ablation element as in claim 14, wherein said trocar member bears said deflection surfaces, said deflection surfaces comprising a number of ramps, said ramps extending partially around said ablation stylets, said ramps being defined proximate the proximal end of said trocar point, the distal ends of said stylets being positionable proximate to said ramps and within said trocar surface, and wherein said stylets are hollow and comprise an alloy comprising nickel and titanium, and have distal ends configured to tangentially engage a respective one of said deflection surfaces.

16. An ablation element as in claim 15, further comprising a graphical user interface and a pair of electrical switches, one of said switches for switching between operating parameter options for the ablation element and the other of said switches for selecting one of said options.

17. An ablation element as in claim 16, wherein a human voice presents options, allowing a surgeon to operate without requiring the surgeon to look away from visual displays guiding the operation, the patient, instruments and so forth, thus removing potential losses of information.

18. An ablation element as in claim 15, further comprising a cooperating low friction insulator ring, for example, made of Teflon, in facing spaced relationship to said deflection surfaces and cooperating with the deflection surfaces to deflect said stylets.

19. An ablation element as in claim 15, wherein an insulation sleeve is positioned between the anchors and the stylets in order to allow separate electrical actuation and ablation with either the anchors or the stylets or both the anchors and the stylets.

20. An ablation element as in claim 1, further comprising anchors deployed by bearing against a deflection surface configured to deploy them in an outward and rearward direction, and wherein said anchors comprise an alloy comprising nickel and titanium.

21. An ablation element as in claim 20, wherein said anchors are made of a springy material which assumes a straight configuration when not subjected to external forces.

22. An ablation element as in claim 20, wherein deflection surfaces for both the hypotube stylets and anchors are configured to result in strains in the range of 3.5% to 4.5%.

23. An ablation element as in claim 1, wherein said stylets which are bound together as a unitary structure and advanced by a single push tube or wire.

24. An ablation element as in claim 1, wherein the stylets contain thermocouples which are connected to measure the temperature of ablated tissue.

25. An ablation instrument, comprising:
(a) an elongated support member having a proximal portion and a distal portion, said elongated support member defining an elongated support member axis;
(b) at least one conductor extending along at least a portion of the length of said elongated support member and mounted for axial movement of at least a portion of said conductor;
(c) a plurality of ablation stylets, each of said stylets being made of metal and having an elongated exposed metal distal portion, said exposed metal distal portion having a length roughly commeasurate with the region to be ablated, said stylets being supported proximate the distal portion of said elongated support member, said stylets comprising a resiliently deflectable material, and said stylets being mounted for axial movement of at least a portion of said stylets;
(d) a head positioned to receive the distal portion of said stylets, said head comprising a head end;
(e) a plurality of alignment channels, each of said stylets each being positioned within a single alignment channel; and
(f) a plurality of open deflection surfaces, each of said open deflection surfaces communicating with a respective alignment channel to receive its respective stylet, said deflection surfaces being positioned proximate said head end and proximate said distal portion of said elongated support member, said deflection surfaces being configured and positioned, in response to advancement of said stylets toward said head end, to deflect at least some of said stylets causing said stylets to exit said deflection surfaces and move along substantially straight external paths external to said head.

* * * * *